(12) United States Patent
Loy et al.

(10) Patent No.: US 12,357,211 B2
(45) Date of Patent: Jul. 15, 2025

(54) STATION FOR URINE ANALYSIS DEVICE, URINE ANALYSIS DEVICE, ASSOCIATED METHODS

(71) Applicant: Withings, Issy les Moulineaux (FR)

(72) Inventors: Jonas Loy, Issy les Moulineaux (FR); Jorys Tiné, Issy les Moulineaux (FR); Marine Kirat, Issy les Moulineaux (FR); Benoît Tucoulat, Issy les Moulineaux (FR); Julius Dewavrin, Issy les Moulineaux (FR); Christelle Barakat, Issy les Moulineaux (FR)

(73) Assignee: Withings, Issy les Moulineaux (FR)

( * ) Notice: Subject to any disclaimer, the term of this patent is extended or adjusted under 35 U.S.C. 154(b) by 0 days.

(21) Appl. No.: 18/688,965

(22) PCT Filed: Sep. 7, 2022

(86) PCT No.: PCT/EP2022/074834
§ 371 (c)(1),
(2) Date: Mar. 4, 2024

(87) PCT Pub. No.: WO2023/036808
PCT Pub. Date: Mar. 16, 2023

(65) Prior Publication Data
US 2024/0268737 A1    Aug. 15, 2024

(30) Foreign Application Priority Data
Sep. 8, 2021    (FR) ........................................ 2109391

(51) Int. Cl.
*A61B 5/20*    (2006.01)
*A61B 5/00*    (2006.01)

(52) U.S. Cl.
CPC ............ *A61B 5/207* (2013.01); *A61B 5/6891* (2013.01)

(58) Field of Classification Search
CPC .................................. A61B 5/207; A61B 5/208
See application file for complete search history.

(56) References Cited

U.S. PATENT DOCUMENTS 9,810,686 B1 * 11/2017 Hall ........................ A61B 5/207
10,383,606 B1 * 8/2019 McCord ............... G01N 33/493
(Continued)

FOREIGN PATENT DOCUMENTS

WO    WO 2021/175909 A2    9/2021
WO    WO 2021/175944 A1    9/2021

OTHER PUBLICATIONS

International Search Report as issued in International Patent Application No. PCT/EP2022/074834, dated Oct. 17, 2022.
(Continued)

*Primary Examiner* — Jacqueline Cheng
*Assistant Examiner* — Tho Q Tran
(74) *Attorney, Agent, or Firm* — Pillsbury Winthrop Shaw Pittman LLP

(57) ABSTRACT

A station for a urine analysis device is proposed, the station including a case, intended to be positioned at least partially within the toilet, a housing, within the case, configured to at least partially receive a cartridge comprising a plurality of test supports (e.g. test strips). The cartridge is movable within the housing. The station may also include an optical sensor, a translatory injector and an analyzer (e.g. optical). Various configurations are available.

23 Claims, 17 Drawing Sheets

(56) References Cited

U.S. PATENT DOCUMENTS

| | | | |
|---|---|---|---|
| 10,921,310 B2* | 2/2021 | Mostafa | G01N 21/77 |
| 2005/0261605 A1* | 11/2005 | Shemer | G01N 21/31 |
| | | | 600/584 |
| 2007/0020143 A1 | 1/2007 | Seidenstricker et al. | |
| 2009/0216099 A1* | 8/2009 | Kim | A61B 5/6887 |
| | | | 600/509 |
| 2013/0324807 A1 | 12/2013 | Kuhr et al. | |
| 2017/0284925 A1 | 10/2017 | Spangenberg et al. | |
| 2018/0184906 A1* | 7/2018 | Prokopp | A61B 5/14507 |
| 2018/0188231 A1* | 7/2018 | Barakat | C12Q 1/001 |
| 2019/0008439 A1* | 1/2019 | Sageder | G01N 33/493 |
| 2019/0293636 A1* | 9/2019 | Tsuruoka | G01N 33/50 |
| 2020/0187863 A1* | 6/2020 | Tu | A47K 13/24 |
| 2020/0205717 A1* | 7/2020 | Yang | E03D 11/13 |
| 2022/0192567 A1* | 6/2022 | Hidas | G01F 23/261 |
| 2023/0105892 A1* | 4/2023 | Barbedette | A61B 10/0012 |
| | | | 600/362 |

OTHER PUBLICATIONS

Written Opinion of the International Searching Authority as issued in International Patent Application No. PCT/EP2022/074834, dated Oct. 17, 2022.

* cited by examiner

STATION FOR URINE ANALYSIS DEVICE, URINE ANALYSIS DEVICE, ASSOCIATED METHODS

CROSS-REFERENCE TO RELATED APPLICATIONS

This application is the U.S. National Stage of PCT/EP2022/074834, filed Sep. 7, 2022, which in turn claims priority to French patent application number 2109391 filed Sep. 8, 2021. The content of these applications are incorporated herein by reference in their entireties.

TECHNICAL AREA

The present disclosure relates to the field of urine analysis devices intended to be positioned inside toilets, either partially or completely. The present disclosure also relates to a method for analyzing urine being received in a toilet.

PREVIOUS TECHNIQUE

Many biological parameters are reflected in an individual's urine. From a urine sample, for example, it is possible to detect health problems such as urinary tract infection, diabetes or kidney failure. A urine sample may also reflect the quality of a diet, identify a fertile period or pregnancy, and detect the use of drugs or tobacco. It is therefore worthwhile monitoring various biological parameters on a regular basis.

It is known to offer devices installed in toilets with a urine analysis function. These devices are capable of taking urine samples from the toilet and analyzing them to determine the level of a biological parameter.

Document US20180188231 discloses a urine analysis device for attachment to a toilet rim. The device uses a field-effect transistor for analysis.

Documents US20170284925 and US10383606 propose devices with test strips running in front of an analysis section.

However, such devices are bulky. In particular, they require a storage area for new and used test strips. These devices must therefore be positioned for the most part outside the toilets, or integrated into them.

Furthermore, such devices are not adaptable. It is particularly difficult to refill new test strips and remove used ones. It is also difficult to perform analyses requiring several types of test strip.

There is therefore a need for a urine analysis device that does not have the disadvantages of the prior art.

SUMMARY

The present description aims to propose one or more solutions resolving at least some of the aforementioned drawbacks. In particular, the applicant has developed a new device comprising a station and a cartridge (also known as a rotary support), described in document PCT/EP2021/055302, the contents of which and those of the priority document are incorporated by reference). The aim of the present application is to propose improvements to the device and station described in that document.

Provided herein is a urine analysis station configured to cooperate with a cartridge to form a urine analysis device. Various methods of using the urine analysis device are also proposed.

In particular, the station comprises a case which is designed to be positioned inside a toilet, i.e. inside the bowl. The case contains the electronics required to operate the station and the device. The main body is positioned to receive a jet of urine when the user urinates. The station may comprise an annular housing, i.e. a ring-shaped empty space, in the case, which extends around an axis of rotation. The station may further comprise a urine injector, positioned in the case, in particular positioned radially inside the annular housing. The annular housing is configured to accommodate, wholly or partially, a cartridge, which is rotatable in the station, about the axis of rotation. The cartridge typically comprises a rotating support which houses a plurality of test supports (e.g. test strips) arranged along an arc of a circle. The test supports are attached to the rotating holder and remain attached to it during use of the urine analysis device. In other words, all test supports, at all times, undergo the same rotational movement when the cartridge is rotated (e.g., in the case of test strips, no winding or unwinding of a strip film around a winder and/or unwinder). As the cartridge rotates in the station, the test supports may thus be selectively positioned in front of the urine injector, which may then inject a controlled volume of urine. To insert the cartridge into the main body, the main body may comprise a removable cover to provide access to the annular housing. The main body may also include an analyzer configured to analyze a test support. In the same way as above, when the cartridge is rotated in the station, the test supports may thus be selectively placed in front of the analyzer, which may then obtain data on the test support facing it. The analysis is typically an optical analysis, such as a colorimetric analysis. In order to correctly position the test support with respect to the injector and/or the analyzer, the station may include a position sensor, which makes it possible to obtain a position, at least locally, of each test support with respect to the case (and therefore with respect to the annular housing). In particular, at least two of the injector, the analyzer and the position sensor are positioned along a radial direction around the axis of rotation at the same place, to work on the same test support without the need to rotate the cartridge between obtaining the position and injecting, or between obtaining the position and measuring, or between injecting and measuring. In this way, injecting and analyzing are optimized.

The test support comprises a reagent capable of reacting once in contact with urine. The reagent may be a dry reagent. In an embodiment, the test support is a test strip, but other supports may be implemented.

Here, "radially" means along a radial direction. Such a radial direction is generally defined as a direction perpendicular to the axis of rotation (A) and passing through the axis of rotation (A).

In an embodiment, the injector is movable relative to the main body. In particular, are defined: an injection position, in which the injector may deposit a few drops of urine on a test support, a purge position, in which the injector may discharge urine to a drain, and a withdrawal position, in which the injector is not configured to be active. During cartridge rotations, the injector is typically in the withdrawal position. In an embodiment, the movement performed by the injector is a translation.

In particular, the injector is positioned radially internal to the annular housing, so that the annular housing surrounds the injector. With the exception of the distal end, which enters the annular housing as the injector moves, the rest of the injector remains radially internal to the annular housing. In certain positions (purge position and injection position), the entire injector remains radially internal to the annular housing. In the purge position, the distal end is even radially external to the annular housing.

The station may also include an electronic control unit ECU and a communication module (typically wireless), for bidirectional communication with a mobile terminal and/or a remote server. A battery in the case supplies power to all components.

This description covers several aspects. Some of these will be highlighted in the following paragraphs, but the description is not limited to them.

In one aspect (referred to as a "curved injector"), a station for a urine analysis device is proposed, the station comprising:
  a case, intended to be positioned inside a toilet,
  an annular housing, about an axis of rotation, in the case, the annular housing being configured to at least partially receive a cartridge mounted for rotation about the axis of rotation in the station and comprising a plurality of test supports,
  an injector, positioned in the case, and configured to inject a controlled volume of urine onto at least one test support, the injector being mounted for translational movement relative to the case.

The injector may comprise a distal injection end which is displaced in translation in a radial or substantially radial direction relative to the axis of rotation.

"Substantially radial" may mean less than 5° either side of the radial direction, or even less than 2°. The closer it is to a radial direction; the more margin are gained in terms of cartridge displacement.

In particular, the injector is positioned radially internal to the annular housing, so that the annular housing surrounds the injector. With the exception of the distal end, which enters the annular housing as a result of the radial displacement, the rest of the injector remains radially internal to the annular housing. In some positions, such as the withdrawal position, the entire injector remains radially internal to the annular housing. In the purge position, the distal end is even radially external to the annular housing.

The injector may be driven in translation along a first axis, while the distal injection end moves in translation along a second axis, called injection axis. The first translation axis is then not confused with the second axis, once these are projected in a plane orthogonal to the rotation axis. By "along a first axis", it is meant that the first axis carries the displacement actuator axis, while the second axis carries the injection axis, the two axes being parallel but offset.

The injector may be curved. In other words, when projected in a plane orthogonal to the axis of rotation, the injector has a curved shape. This means that the fluid-carrying channel of the injector is curved.

The case may include a central mechanical coupler, on the axis of rotation, able to cooperate with the cartridge to rotate the latter. The second translation axis may then pass through the mechanical coupler, and the first translation axis may be offset from the mechanical coupler. The curved shape of the injector bypasses the mechanical coupler. Typically, the second axis of translation is separated from the first axis by a given offset distance (e.g. at least 5 mm and less than 15 mm or even 10 mm).

The injector may comprise a proximal end, opposite the distal end and configured to receive urine. The distal end and the proximal end are then connected to each other by an intermediate portion comprising two successive inverted bends. In particular, the bend closest to the distal end (distal bend) has a smaller radius of curvature than the bend closest to the proximal end.

The injector may be rigid.

The station may include a displacement actuator, configured to move the injector, particularly in translation.

For translational movement of the injector, the injector may be integral with a nut suitable for receiving a threaded spindle driven in rotation by the displacement actuator. The injector may also be mounted on a carriage, and the carriage may take up the forces transmitted by the displacement actuator. For example, the carriage is driven in translation along the first axis. The nut may be mounted on the carriage.

The carriage may comprise a guide configured to cooperate with a guide of the case to guide the carriage in translation. A sliding link is provided to compensate for the parasitic torque generated by the offset between the injection axis and the displacement actuator axis.

The case may comprise a urine collector, the collector being fluidly connected to the injector, in particular via the proximal end. The case may comprise an electronic control unit, the electronic control unit thus being received in the case.

The station may comprise an analyzer (e.g. an optical analyzer), positioned at least partially radially outside the annular housing and configured to optically analyze at least one test support. The analyzer may be positioned facing the distal end of the injector (when projected in a plane orthogonal to the axis of rotation).

In one aspect (referred to as "position sensor and injector"), a station for a urine analysis device is proposed, the station comprising:
  a case, intended to be positioned inside a toilet,
  an annular housing, about an axis of rotation, in the case, the annular housing being configured to at least partially receive a cartridge mounted for rotation about the axis of rotation in the station and comprising a plurality of test supports,
  an injector, positioned in the case, and configured to inject a controlled volume of urine onto a test support, when the strip is positioned in an injection zone of the annular housing,
  a position sensor, configured to obtain the position of a marker associated with a test support of the cartridge when the marker is positioned in the injection zone or in a proximity zone of the injection zone.

The term "injection zone" refers in particular to an angular sector in the reference frame around the axis of rotation. The injector and the position sensor are therefore arranged to interact with the same test support, without rotation of the cartridge between obtaining the position and injecting. In particular, the marker may be a test support directly.

The injection zone may correspond to the angle occupied by a single test support (in angular window equivalent). For example, the injection zone may correspond to an angular window of less than 5°, or even less than 2° on either side of the radial direction.

The proximity zone of the injection zone may correspond to an angular sector of less than 30° on either side of the injection zone (from the edges of the injection zone), or even less than 20°, or even less than 10°, or even less than 5°.

The injector may comprise a distal injection end and the position sensor is radially aligned (by projection in a plane orthogonal to the axis of rotation) with the distal end of the injector. The injector and position sensor may be offset along the axis of rotation (by projection onto the axis of rotation).

The position sensor may be positioned at least partially radially outside the annular housing.

The case may include an analyzer configured to analyze at least one test support. In particular, the analyzer is an optical analyzer.

The injector may be configured to inject into an injection zone of the annular housing and the analyzer is configured to measure data in an analysis zone, the injection zone and the analysis zone being coinciding. The analyzer may be positioned radially facing the distal end of the injector (when projected in a plane orthogonal to the axis of rotation). The position sensor may be the analyzer (same equipment but different function). The injector may be mounted so as to move in translation relative to the case along a translation direction, in order to get closer to and/or pass through the annular housing.

The position sensor may alternatively or additionally comprise a mechanical follower, such as a cam follower (which cooperates with the cartridge) or an electromagnetic module (which cooperates with a magnetic element of the cartridge).

In one aspect (referred to as "analyzer and injector"), a station for a urine analysis device is proposed, the station comprising:
a case, intended to be positioned inside a toilet,
an annular housing about an axis of rotation, positioned in the case, the annular housing being configured to at least partially receive a cartridge mounted for rotation about the axis of rotation in the station and comprising a plurality of test supports,
an analyzer, mounted in the case, and configured to obtain information relating to the test support after urine injection, when the test support is in an analysis zone of the annular housing,
an injector, mounted in the case, and configured to inject a controlled volume of urine onto a test support, when the test support is in an injection zone of the annular housing.

The analysis zone and the injection zone are coinciding. In this way, there is no need to rotate the cartridge between injecting and measuring by the analyzer. The analyzer and injector are therefore angularly located at the same place around the axis of rotation (possible offset along the axis of rotation).

The station also includes a position sensor, configured to obtain the position of a marker associated with a test support of the cartridge, when the marker is positioned in the analysis zone or in a proximity zone of the analysis zone. The proximity zone of the analysis zone may correspond to an angular sector of minus 30° on either side of the injection zone, or even 20°, or even 10°, or even 5°. The analysis zone may correspond to an angular sector less than or equal to the angle occupied by a single test support.

The injector may be mounted for translational movement in the case.

The station may comprise a memory and a processor, the memory comprising instructions configured to implement the following steps:
(E3) injecting urine onto a test support by the injector,
(E4) measuring on the test support by the analyzer.

In particular, the instructions do not include rotating the cartridge between the injecting step (E3) and the analyzing step (E4). The instructions may include that the measuring step (E4) starts before the end of the injecting step (E3), for example two seconds before the end or as soon as the first drop of urine is injected, or even before the first drop of urine is injected. This makes it possible to obtain measurements relating to the kinetics of the reactions taking place on the test support brought into contact with the urine.

Also proposed is a method of urinalysis using the urinalysis device as described above, comprising the following steps:
(E3) injecting urine onto the test support,
(E4) measuring on the test support by the analyzer,
wherein the cartridge is not rotated between the injecting step and the analyzing step.

In one aspect (referred to as "direct measurement of test support position"), a station for a urine analysis device is proposed, the station comprising:
a case, intended to be positioned inside a toilet,
a housing, in the case, configured to at least partially receive a cartridge comprising a plurality of test supports, the cartridge being movably mounted inside the housing,
a position sensor, configured to directly measure the position of a test support of the cartridge in the annular housing, i.e. relative to the case.

In particular, the position sensor does not measure the position of the cartridge, or more specifically, the position of the rotary support of the cartridge or of the separator. Thus, any inaccuracy in positioning the test support on the rotating support is overcome by directly retrieving the position of the test support in the annular housing.

The position sensor may comprise a light source and an optical sensor, the light source being configured to emit light towards a test support and the optical sensor being configured to receive the light.

The station may comprise an analyzer, the analyzer working in an analysis zone of the case, and the position sensor is configured to directly measure the position of a test support located in the analysis zone. In particular, the analyzer may be angularly located at the same position as the optical position sensor (with or without offset along the axis of rotation A). The analysis zone may correspond to an angular sector less than or equal to the angle occupied by a single test support.

The analyzer may be the position sensor. In other words, the hardware forming the analyzer may be used as a position sensor.

The housing may be an annular housing, about an axis of rotation, in the case, the annular housing being configured to at least partially receive a cartridge mounted for rotation about the axis of rotation in the station.

The position sensor may see test supports scrolling past when the cartridge is set in motion, and is able to receive a signal that varies according to whether or not a test support is present facing the position sensor. The station may further comprise an electronic control unit with a processor and memory. The electronic control unit may be in the case. The memory may include instructions which, when executed by the processor of the electronic control unit, cause the following steps:
(F1) scrolling the test supports in one direction,
(F2) analyzing the evolution of the signal during scrolling,
(F3) identifying a local extremum,
(F4) in response to said identifying, scrolling the test supports in the opposite direction,
(F5) positioning the test support which generated the first extremum.

Positioning (F5) may comprise:
after the test supports have been reversed (F4), (F51) identifying a value in the vicinity of the local extremum value, (F52) stopping the reverse movement of the test supports.

Identifying the local extremum (F3) consists in obtaining at least three return signal values, corresponding to three different positions of the cartridge in the station, and finding the intermediate value to be the highest, so that when the local extremum is identified, the test support is no longer facing the position sensor.

When the housing is an annular housing, scrolling may be rotating the cartridge.

The case may include an injector, configured to inject urine onto the test support which is identified as being in position by the position sensor.

The station may include a drive actuator, e.g. a stepper, for moving the cartridge. A signal value may be obtained at each step.

Also proposed is a method of positioning a test support using the device comprising a station as described above and a cartridge. The method includes a step of measuring the position of a test support directly. More specifically, the method comprises the following steps:
(F1) scrolling the test supports in one direction,
(F2) analyzing the evolution of the signal during scrolling,
(F3) identifying a local extremum,
(F4) in response to said identifying, scrolling the test supports in the opposite direction,
(F5) positioning the test support which generated the first extremum.

The present description also covers a urine analysis device comprising a station (as described in the various aspects above) and a cartridge. The cartridge is then configured to be at least partially received in the annular housing of the case. Each test support is integral with the cartridge and is configured so that it may be selectively positioned in front of the position sensor, the injector and the analyzer. In particular, the test support is a test strip. The present description also covers a kit comprising this station and a cartridge or a plurality of cartridges (cartridges with different types of test supports).

BRIEF DESCRIPTION OF THE DRAWINGS

Further features, details and advantages will become apparent from the detailed description below, and from an analysis of the appended drawings, on which.

DESCRIPTION OF EMBODIMENTS

Figure 1:
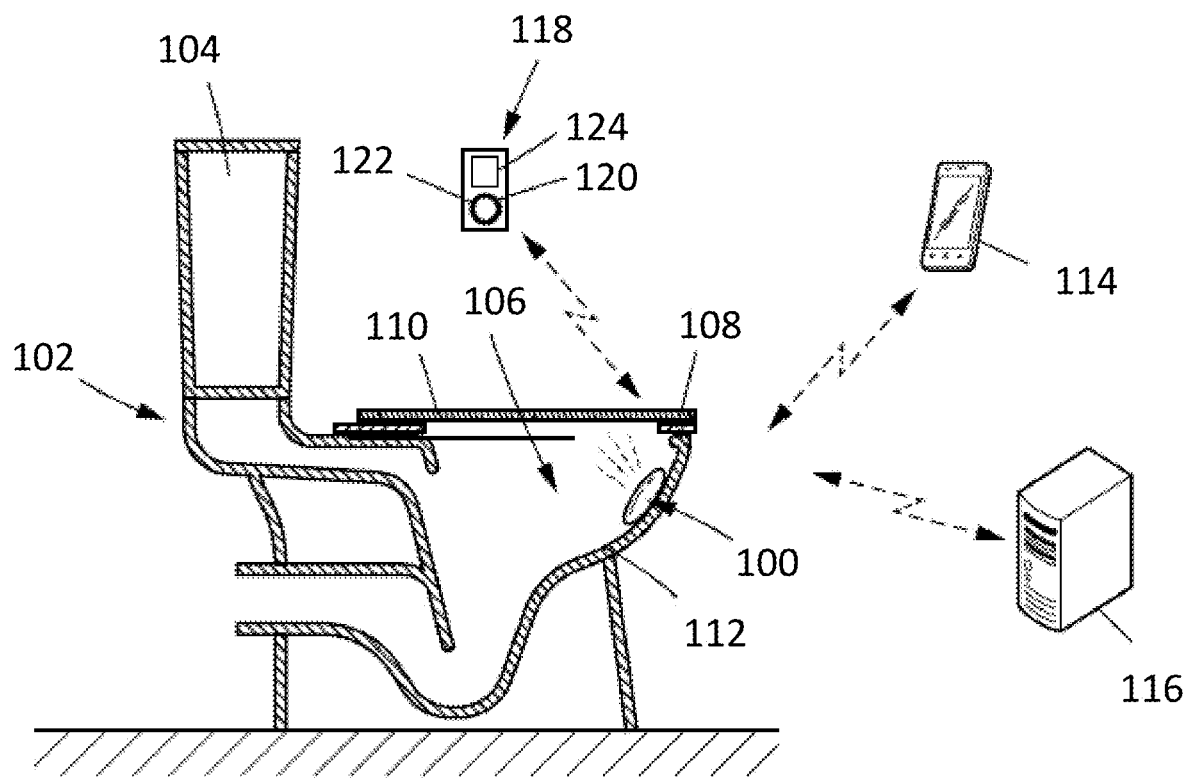
FIG. 1. This figure schematically represents a cross-sectional view of a toilet equipped with a urine analysis device in the sense of the invention.

FIG. 1 schematically illustrates a urine analysis device 100 mounted on a toilet 102. The toilet 102 comprises a water tank 104, a toilet bowl 106, a seat 108 and a toilet lid 110. The urine analysis device 100 is mounted on an inner wall 112 of the toilet bowl 106. Advantageously, the urine analysis device 100 is entirely located in the toilet bowl, making it discreet.

The urine analysis device 100 may be positioned in the path of a urine stream secreted by a user. The urine analysis device 100 receives a stream of urine when a user urinates in a seated position in the toilet. The position of the urine analysis device is then adapted for any type of user, male or female, regardless of age. The user may then urinate in the toilet without worrying about the position of the urinal.

Urine analysis device 100 may also be positioned in the path of a flush from cistern 104. In this way, the urine analysis device 100 may be flushed when the toilet is flushed. The urine analysis device 100 is hygienic.

The urine analysis device 100 may communicate with a mobile terminal 114 (such as a smartphone) and/or an external server 116. In an embodiment, the urine analysis device 100 communicates with the mobile terminal 114 (for example directly via Bluetooth such as Bluetooth Low Energy) and the mobile terminal 114 communicates with the server 116 (via a cellular or WiFi connection). In another embodiment, the urine analysis device 100 may communicate directly with the server 116 via a cellular network.

To initiate a measurement by the urine analysis device 100, an external activator 118 may be provided. The external activator 118 may comprise a button 120 and/or a biometric sensor 122. A display 124 may be installed on the external activator 118 to display the data obtained by the urine analysis device 100. The urine analysis device 100 and the external activator 118 communicate wirelessly.

Figure 2:
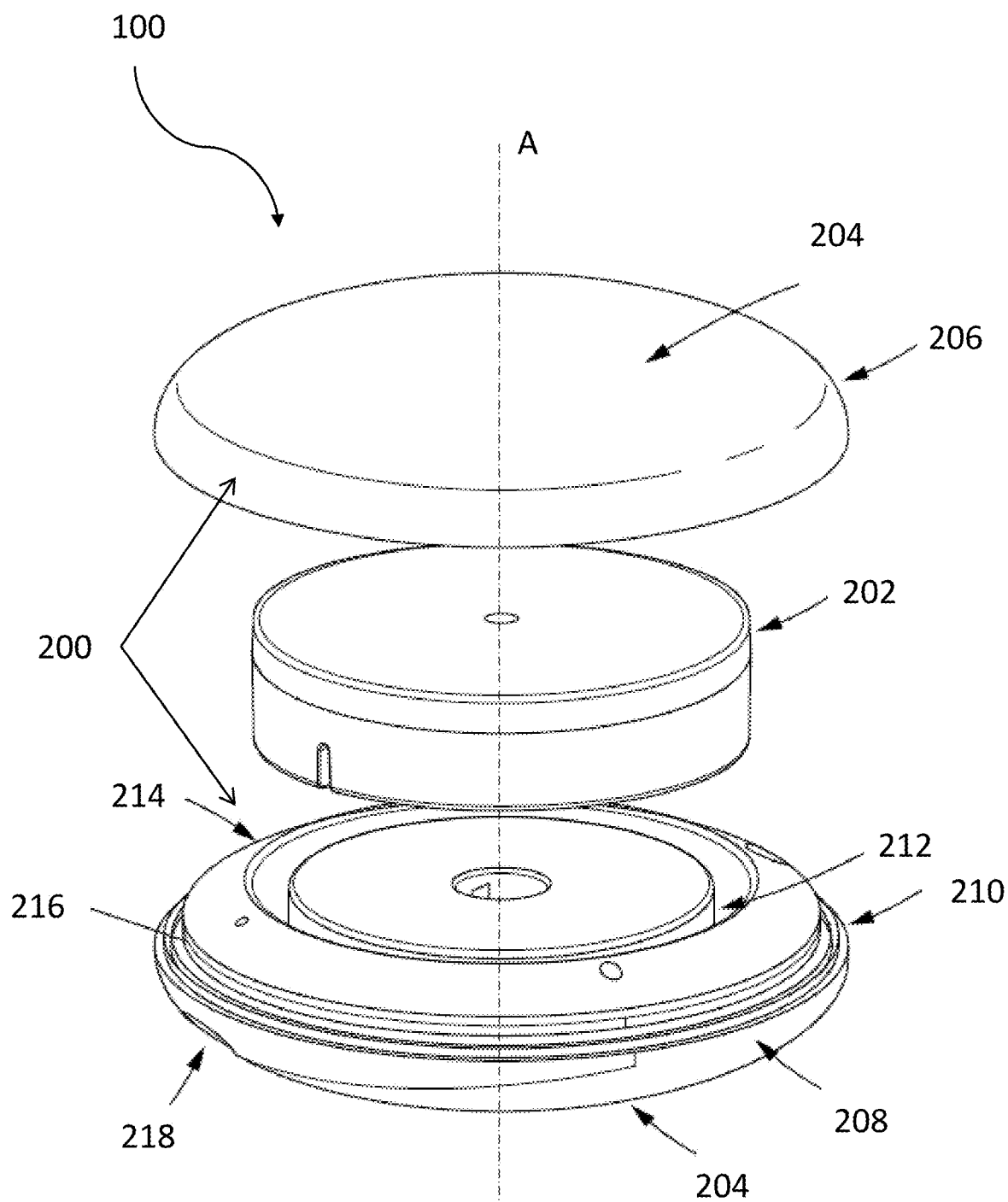
FIG. 2 This figure shows an exploded view of a urine analysis device.

As shown in the exploded view in FIG. 2, the urine analysis device 100 comprises a station 200 and a cartridge 202, removably mounted in the station 200. In particular, the station 200 comprises a case 204 which, according to one particular embodiment, is formed as an assembly of two half-shells: a front shell 206 and a rear shell 208. The front and rear shells form a joint 210 of the case, in a plane normal to axis A. Urine analysis device assembly is facilitated when the case consists of the front and rear shells. Case 204 contains a test assembly (not visible in FIG. 2, but visible in FIG. 6). The test assembly is intended to analyze the urine being received in the urine analysis device 100. Station 200 further comprises an annular housing 212, inside case 204, arranged around an axis of rotation A. The annular housing 212 is configured to at least partially receive the cartridge 202 mounted for rotation about the axis of rotation A (once in position in the annular housing 212). The cartridge 202 comprises a plurality of reagent-integrating test supports, for example a dry reagent, arranged along a circle or arc of a circle around the axis of rotation A. In an embodiment and for the remainder of the description, the test supports are test strips. In particular, the annular housing 212 may be partially delimited, with functional clearance, by an inner cover 214, mounted for example with the rear shell 208, to protect components of the test assembly. The inner cover 214 may comprise a radially outer portion, to protect components radially external to the annular housing 212, and a radially inner portion, to protect components radially internal to the annular housing 212.

The annular housing 212 typically extends over 360° and forms a groove configured to partially receive the cartridge 202.

In the present description, the term "radially internal to the annular housing" means closer to the axis of rotation A than the annular housing is close to the axis of rotation A. Similarly, the term "radially external to the annular housing" means "further away from the axis of rotation A than the annular housing is from the axis of rotation A".

The annular housing 212 may be accessed, for example, by detaching the front shell 206 from the rear shell 208. The front shell 206 and rear shell 208 may be screwed together using a thread 216.

The station 200, in particular the case 204, also includes a collection port 218, positioned for example on the rear shell 208 in FIG. 2. Collection port 218 may receive urine flowing by gravity over the outer surface of case 204. More details on this collection port 218 will be given later.

The case 204 is removably arranged in the toilet bowl 106. The analysis device 100 may then be removed or repositioned in the toilet. In addition, the urine analysis device 100 or the case 204 may be removed to recharge a battery or to change the cartridge 202.

In the example shown in FIG. 2, the case 204 is arranged on the inner wall 112 of the toilet. The case 204 is positioned by a fastening element 300, an example of which may be seen in FIG. 3. The fastening element 300 may comprise magnets 302 and/or an adhesive/suction cup surface which may cooperate. This configuration enables the case to be easily removed or repositioned in the toilet. In another configuration, the urine analysis device 100 comprises a hook attached at one end to the case 204 and configured to attach at the other end to a rim of the toilet bowl 106 (under the seat 108, for example).

Figure 3:
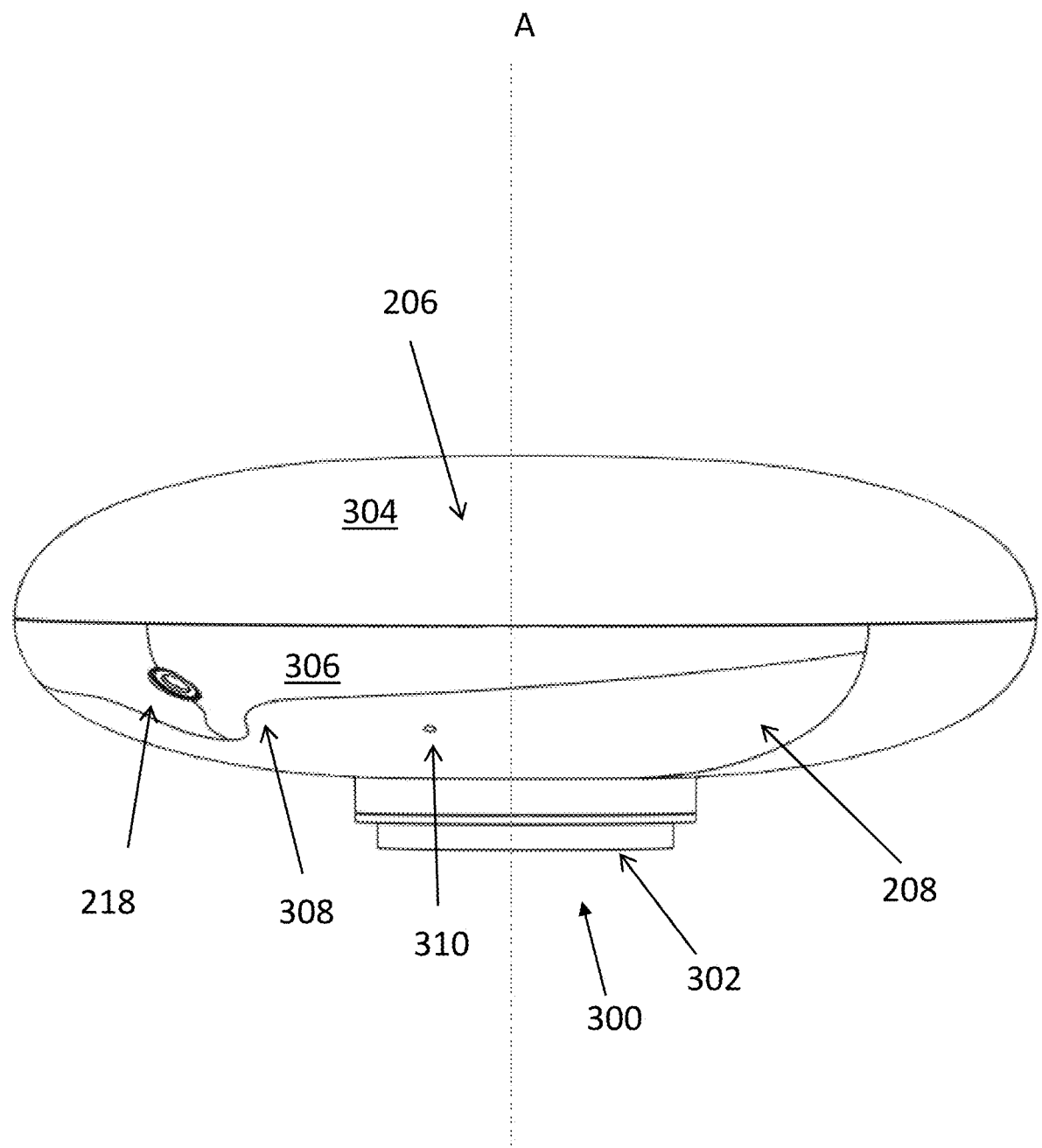
FIG. 3 This figure shows a side view of a urine analysis station or device according to an embodiment.

The station 200, in particular the case 204, also includes a drain port 310, positioned on the rear shell 208 in FIG. 3. The collection port 218 may receive urine flowing by gravity over the outer surface of the case 204, and the drain port 310 enables the various fluids collected by the device 100 to be drained off. Further details of this drain port 310 will be given later.

General Characteristics Of The Case

Figure 4:
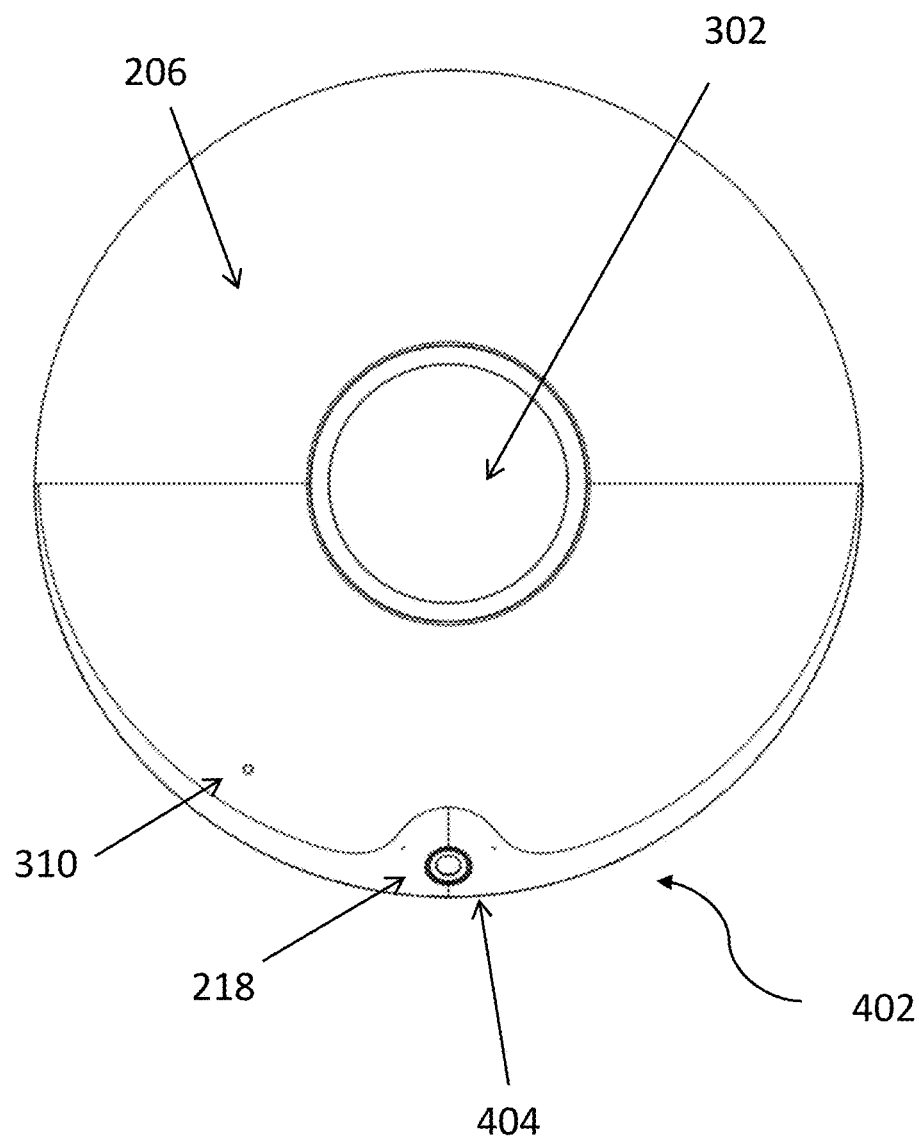
FIG. 4 This figure shows a view of the rear side of a urine analysis station or device according to an embodiment.

As shown in FIGS. 2 to 4, case 204 has the external shape of a circular pebble. In other words, the case has the shape of a flattened spheroid. The axis of rotation A is the central axis of the case. The case has a front 304 and a rear 306 face, substantially normal to axis A. The front face 304 typically comprises the outer surface of the front shell 206 and the rear face 306 notably comprises the outer surface of the rear shell 208. In this way, urine may be collected directly from faces 304, 306 of the case. Case 204 serves as a urine collector.

The front face 304 faces the inside of the 106 bowl. The front face 304 is then intended to receive urine when the user urinates in a seated position on the toilet. The rear face 306 faces the inner wall 112 of the bowl 106. The front face 304 and rear face 306 are connected by curved edges 308. Thus, the outer surface of case 204, consisting of front face 304, rear face 306 and curved edges 308, is defined by curved lines, forming a generally convex object. For example, the case has no edges. Urine may run down the entire outer surface of the case without coming off the case or forming air bubbles, which could compromise urine analysis. Application PCT/EP2021/055377 describes in detail the shape of case 204 for efficient urine collection.

In an embodiment, case 204 has a diameter, measured in the direction normal to axis A, comprised between 50 mm and 150 mm, for example close to 100 mm. Case 204 also has a thickness, measured in the direction of axis A, of between 15 mm and 50 mm, for example around 30 mm. In this way, the case is sufficiently compact to be fully accommodated in the toilet bowl. The urine analysis device is discreet. In addition, the case is sufficiently big to systematically come into contact with urine being received in the toilet bowl. The user may then urinate in the toilet without worrying about the urine analysis device, or at least aim summarily.

The outer surface of the case is smooth. In this way, the jet of urine coming into contact with the case clings to and spreads over the outer surfaces of the case. In an embodiment, the case is made of a hydrophilic material. For example, the case may be made of one of the following: ceramic, polyamide (PA), silicone or a hydrophilic polymer. The outer surface of the case may also be treated with a hydrophilic surface treatment, for example acuWet® from Aculon, a hydrophilic polymer, or Pebax® from Arkema.

The front shell 206 and rear shell 208 are joined together to maintain the outer surface of the case defined by curved lines. The joint 210 between the front shell 206 and the rear shell 208 allows urine to run off between the front and rear surfaces. This minimizes the impact of the joint on urine run-off on the case.

Alternatively to screw fastening, the front shell 206 and rear shell 208 may be assembled by gluing, clipping, magnetizing, bayoneting or ultrasonic welding. Of course, other fastening methods may also be used to assemble the front and rear shells. In the case of screw fastening, an internal portion of the front shell has a thread. The thread of the front shell is designed to cooperate with a thread of the rear shell, or vice versa. In this way, the case may be easily disassembled to gain access to the test assembly inside the case.

A seal may be present at the joint 210 between the front and rear shells. In this way, the case is watertight. The interior of case 204 is impermeable to urine, water from water tank 104 or toilet 106, and any other type of contaminant. Only collection and drain ports connect the outside and inside of the case, as described in greater detail below.

In a non-illustrated embodiment, the front shell 206 or rear shell 208 includes a removable cover enabling the cartridge 202 to be replaced. Rather than disassembling the front shell 206 to access the annular housing 212, the removable cover simply needs to be removed.

The removable cover may be attached to the rear shell 208 by clipping, screwing or a bayonet mechanism. Of course, other means of attachment may be used to secure the removable cover to the rear shell 208. Alternatively, in another example, the removable cover could be attached to the front shell 206.

The removable cover is sealed. For example, a joint between the removable cover and the rear shell 208 may comprise a gasket. This ensures that the interior of case 204 remains impervious to urine, water from water tank 104 or bowl 106, and any other type of contaminant.

In the example shown in FIG. 2, as already mentioned, the removable cover is formed by the front shell 206 of the case 204. The removable cover may then be removed by unscrewing the front shell 206 from the rear shell 208. The housing 212 has fewer joints that may be soiled and/or infiltrated by toilet water.

The case 204 features a collection port 218, already shown in relation to FIG. 2. The collection port 218 may receive urine flowing by gravity over the outer surface of the case. Urine is collected directly from the sides 305, 306 of the case.

Collection port 218 is located on a lower end 402 of case 204. The lower end 404 faces the bottom of the toilet bowl 106 when the case 204 is positioned in the toilet bowl 106. This position corresponds to normal use. In this position, urine is collected by gravity over most of the outer surface of the case.

In this case, a distance D separating the collection orifice 218 from a lower edge 404 of the case is less than 40 mm, for example less than 20 mm. In a particular embodiment, the collection port 218 is arranged a few millimeters above the bottom edge of the case. Alternatively, the collection port may be on the bottom edge 404.

The collection port 218 is a circular opening, for example with a diameter of between 0.3 mm and 2 mm. The diameter of the collection orifice may be chosen to maximize the volume of urine collected from the outer surface of the case.

The case 204 has a drain port 310, already shown in connection with FIG. 4. The drain port 310 is used to purge excess urine from the urine analysis device 100.

The drain port 310 is separate from the collection port 218. Drain port 310 is also located on the lower end 404 of case 204, adjacent to collection port 218. Drain port 310 is also a circular opening. Drain port 310 has a diameter of between 0.3 mm and 2 mm. In the normal position of use, the drain port 310 may be located above the collection port 218 without cross-contamination.

The drain port 310 may also be positioned away from the collection port 218. The position of drain port 310 may be chosen to facilitate access to the drain port by test assembly.

Alternatively, the drain port may be the same as the collection port. A single port limits the number of openings to the inside of the case. This reduces the risk of introducing contaminants or elements likely to clog the test assembly.

The collection port 218 and the discharge port 310 may be fitted with a metal mesh filter. The average mesh opening of the filter is, for example, 20 microns. The filter prevents the introduction of contaminants or elements likely to obstruct the test assembly, and filters the urine received in the collection port.

In the examples shown, the collection port 218 and the discharge port 310 are located on the rear side 306 of the case (on the rear shell 208). The collection port 218 and discharge port 310 face the inside wall of the toilet bowl when the urine analysis device 100 is positioned in the toilet. In this position, the collection port and discharge port are concealed by the front face of the case. This position also prevents the introduction of contaminants or elements likely to obstruct the test assembly.

The case 204 is not limited to the embodiments described above in relation to the figures, but is, on the contrary, susceptible to numerous variants accessible to the person skilled in the art.

In particular, the case may take any geometric shape defined by curved lines. In particular, it may have a diamond or inverted teardrop shape. In this case, the case has a point on the lower part to guide urine towards the collection orifice.

The collection port and drain port may be located on the front of the case. In this way, urine running down the front reaches the collection port more directly.

The collection port and discharge port may be located on a positive relief, such as a projection, or a negative relief, such as a gutter or recess. Generally speaking, the relief may be of any geometry to channel urine running down the case and convey it to the collection port without detaching from the case or forming air bubbles.

In one example, the collection port 218 is located on the front face 304, while the drain port 310 is located on the rear face 306.

Test Assembly (Injector and Analyzer)

A cartridge and a test assembly for using the cartridge's test supports, such as test strips (e.g. colorimetric strips or lateral flows), will be described (more details at the end of the description). Strips are also referred to here as "test strips" or simply "strip". The test assembly includes an injector and an analyzer (e.g. an optical analyzer). The cartridge 202 is rotated in the case 204 by a drive actuator, positioned in the case 204, so that the test strips may pass in succession in front of the injector and the analyzer. The test assembly also includes a position sensor, to identify a position of the test strips in the case. The position sensor may be used to identify the strip position locally (and not necessarily in absolute terms). Depending on the embodiment, and in particular the embodiments that will be described later, the injector, the analyzer and/or the position sensor may be positioned in the case 204 at the same angular location or at different angular positions, either radially internal or external to the annular housing 212.

The injector is able to inject a controlled volume of urine onto a strip when the strip is in an injection zone ZI of the annular housing 212. The ZI injection zone corresponds to an angular window (around the axis of rotation) of the annular housing 212 within which the injector is able to inject urine onto the strip.

The analyzer is able to analyze a strip when the strip is within an analysis zone ZA of the annular housing 212. The analysis zone corresponds to an angular window or sector (around the axis of rotation) within which the analyzer is able to take measurements on the strip.

The position sensor is able to obtain a position of the cartridge or strip when a marker associated with it is within a control zone ZC. The control zone ZC corresponds to an angular window or angular sector (around the axis of rotation) within which the position sensor is able to obtain a position of the cartridge or strip. In particular, the position measurement obtained by the position sensor is used to drive the drive motor (feedback loop). In an embodiment, the position sensor may enable the station to know that a strip is in the control zone, but not necessarily to know which strip it is. In another embodiment, the position sensor, coupled with a displacement counter from a zero position (described later), may be used to determine exactly which strip is in the control zone.

Depending on the methods described below, the injection zone ZI, the analysis zone ZA and/or the control zone ZC may be coinciding, partially coinciding or separate.

In particular, the analyzer may detect a color change of the test support, which may be a strip (colorimetric analysis). The analyzer may then be an optical analyzer, with a light source and an optical sensor.

Cartridge

Figure 5:
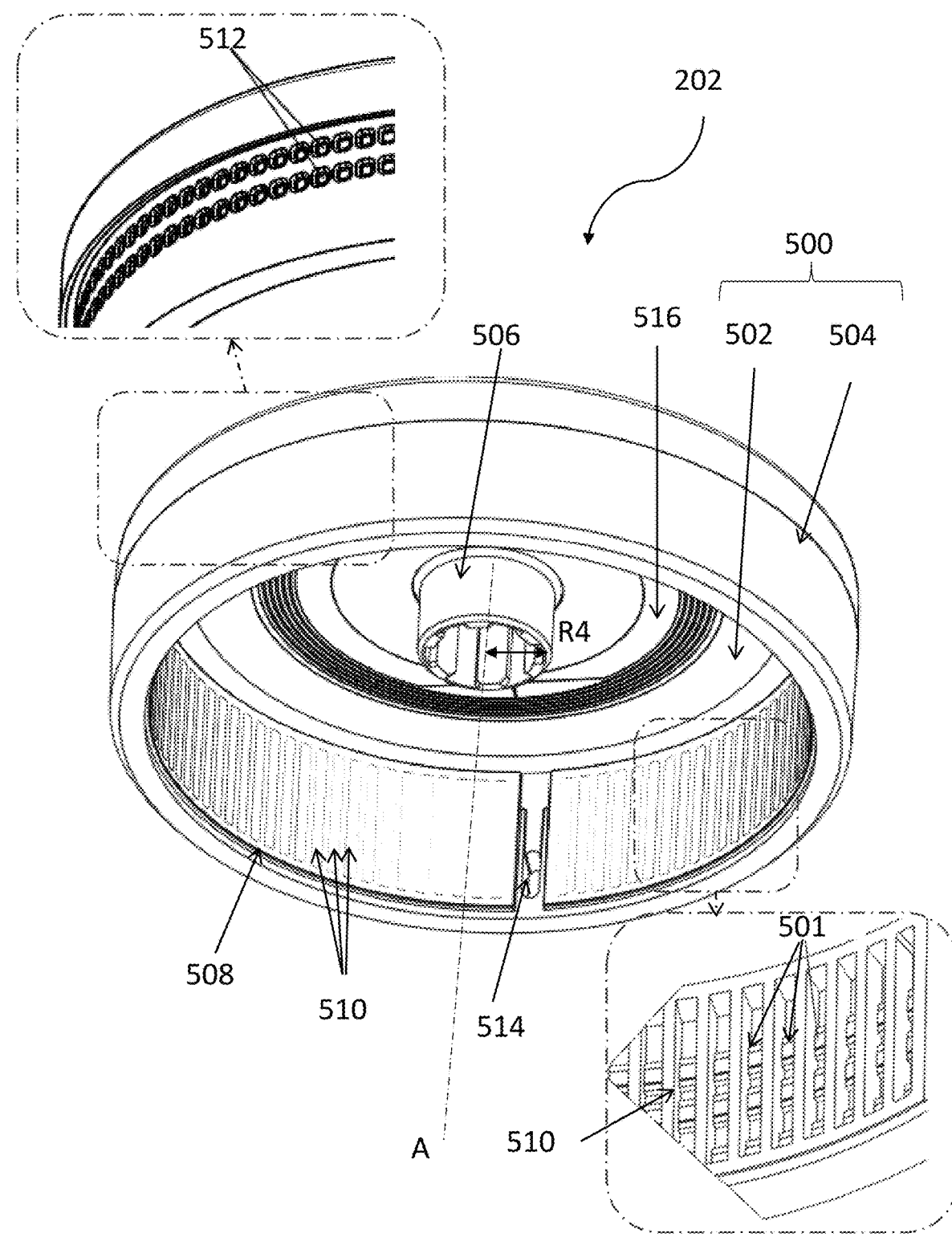
FIG. 5 This figure shows a cartridge cooperating with the station to form a urine analysis device, with a partial view without the cylindrical portion for a better view of the separator.

FIG. 5 shows an exploded view of the cartridge 202. Cartridge 202 incorporates test supports designed to receive urine when cartridge 202 is mounted in station 200 and, in particular, in annular housing 212. The test support comprises a reagent which reacts when in contact with urine. As illustrated in the figures and as shown, the test supports may be test strips 501 (for the remainder of the description we will refer to them as test strips). The cartridge 202 comprises a rotatable support 500, configured to be rotated by the station 200. In normal use of the cartridge 202 and the urine analysis device 100, the test strips 501 remain mounted in the rotatable support 500 and do not move relative to it. In particular, the strips 501 are not rolled up on the rotary support 500 for use: they are thus not unrolled during use.

In an embodiment, the rotary support 500 has a hollow cylindrical shape extending annularly around an axis which, when the cartridge 202 is mounted in the station 200, is the median axis A of the case 204 (for linguistic convenience, a single axis A will be used to describe the various elements, referred to as the axis of rotation A). In practice, the rotary support is generally rotationally symmetrical about the axis of rotation A. The rotating support 500 may store a large number of test strips 501, yet is compact enough to fit inside the case 204.

The cartridge 202 and the rotating support 500 as shown in the figures extend over a full turn and may make a complete revolution in station 200. However, it may be possible, for reasons of space or to free up space for other components, to have a cartridge 202 which extends over a portion of a revolution (e.g. less than 180° or 90°) and which rotates only a portion of a revolution (e.g. less than 270°). In this case, the number of strips is typically lower than for the urine analysis device shown in the figures.

The strips are arranged in a circle or a portion of a circle, for example at one radial end of the rotating support 500 to maximize their number (the larger the radius, the larger the perimeter for installing strips). Positioning in a circle ensures that the strips 501 are all at the same distance from the axis of rotation A and, therefore, from the injector or analyzer (in particular an optical sensor of the analyzer, which will be described later). This also ensures that the measurement protocol for each strip is identical. As illustrated in the figures, strips 501 may be arranged generally in a circular or arc of a circle arrangement. In this way, strips 501 may be equidistant from the axis of rotation A. More specifically, each of the strips 501 may be a small, thin, narrow strip that extends in its longitudinal direction parallel to the A axis. In this way, strips 501 are arranged parallel to one another.

In shape and function, cartridge 202 is similar to a barrel. In one example, the cartridge substantially occupies the annular volume provided by the annular housing 212. A small functional clearance is provided to enable the cartridge to rotate without rubbing against the walls of annular housing 212.

In this case, an outside diameter of the rotating support 500 may be between 30 mm and 130 mm, preferably around 60 mm. A height of the rotary support, measured in the direction of axis A, may be between 12 mm and 40 mm, preferably around 14 mm. A ratio between the diameter of the rotating support and the diameter of case 204 may be greater than or equal to 0.3, preferably greater than or equal to 0.5. This provides a very compact solution for the large number of test strips available.

The rotary support 500 comprises an annular portion 502 and a cylindrical portion 504, extending from an outer radial end of the annular portion 502. The cylindrical portion 504 typically extends from a single side of the annular portion 502 and is configured for insertion into the annular housing 212 of the case 204. The strips 501 are positioned along the cylindrical portion 504 (oriented parallel to the axis of rotation A), so as to be able to run selectively and/or successively in front of the injector and analyzer. The annular portion 502 remains outside the annular housing 212 and serves to stiffen the cylindrical portion 504 and/or enable the cartridge 202 to be driven in rotation.

To this end, the annular portion 502 may further comprise a mechanical coupling 506 configured to engage with a mechanical coupling of the station 200, for example a female attachment sleeve configured to engage with a shaft driven in rotation by the motor, or a male attachment shaft configured to engage a female sleeve driven in rotation by the motor. In the example shown in the figures, a drive pinion 602 (visible in FIG. 6) is provided at the gearbox output, and the female portion is formed by the hub 506 of the rotary support 500.

In an embodiment, the mechanical coupling 506 is arranged on the axis of rotation A of the rotary support 500. However, in the example where the cartridge 202 is rotated via a coupling on the cylindrical portion, the annular portion 502 may be devoid of the female sleeve 602. The annular portion 502 could be mounted by any type of pivoting connection with respect to the case 204. The annular portion 502, with the exception of the mechanical coupler 506, when it passes through, at axis A, may resemble a disk. The female sleeve and hub may be inverted.

In an embodiment, cartridge 202 comprises a separator 508 with chambers 510 for receiving strips 501. The chambers 510 and the strips 501 have similar dimensions, which will be given at the end of the description.

The separator 508 is, for example, a flexible part, in particular made of elastomer, in the form of a strip or ribbon designed to be wound into the rotating support 500. The separator 508 extends along a longitudinal direction and may be wound against an inner wall of the annular portion 504 of the rotary support 500. Separator 508 comprises a first face comprising a plurality of chambers 510 each receiving one or more test strips 501. The first face may be covered by a cover to protect the strips when not in use. The separator 508 comprises a second face comprising, facing each chambers 510, at least one through hole 512 (for example two, as illustrated in the transparent view of the annular portion 504). The chambers 510 are thus sealed. Thanks to the flexible separator 508, the test strips 501 may be inserted into the chambers 510 on a flat surface, simplifying assembly. Once the separator 508 has been installed, the chambers 510 extend parallel to the direction of rotation A.

The cylindrical portion 504 is transparent, or comprises transparent zones, particularly facing the chambers 510. The cylindrical portion 504 is in contact with the separator 508, in particular the second face of the separator 508. During colorimetric analysis, light may pass through the cylindrical portion 504, via the through-hole 512, to analyze the test strips.

In particular, the cylindrical portion 504 may be made of polycarbonate. Polycarbonate has good light transmission properties, while remaining relatively inexpensive and compatible with an injection molding process.

The annular portion 502 of the rotating support 500 forms a base to support the separator 508. The cylindrical portion 504 receives the separator 508. The separator 508 is locked in translation along direction A by contact with the annular portion 502. On the other side, an annular flange extending from one end of cylindrical portion 504 and radially inwards blocks translation in the other direction A.

The rotating support 500, and more particularly the cylindrical portion 504, also includes a through-going purge opening 514 to allow the injector to pass through the cartridge 202 and the annular housing 212 and join a station discharge circuit. Separator 508 does not cover the purge opening 514. This circuit will be described in detail later.

Cartridge 202 also includes an identifier 516, shown in FIG. 5 as an RFID chip. The identifier 516 enables station 200 to know which cartridge 202 has been inserted. The identifier 516 is typically a passive RFID tag.

According to another, non-illustrated example, the rotating support 500 could be a washer, whose axis coincides with the median axis A of the case. The washer then extends radially, in a plane substantially normal to the median axis A of the case. The test strips may then be stored on one side of the washer, normal to axis A. In particular, this configuration enables the rotary support to be adapted to different case shapes. In this way, the rotating holder may be implemented in a variety of urine analyzers.

Each chamber 510 may accommodate a single test strip. All test strips 501 in chambers 510 may be of the same type. By same type, we mean that they are sensitive to the same compounds contained in urine. The cartridge 202 is then adapted for a specific analysis.

Alternatively, the test strip 501 received in chamber 510 may be of a different type from the test strip received in the adjacent chamber. In this way, several types of analyses, requiring different types of test strip, may be carried out using the same cartridge 202.

Alternatively, each chamber 510 may contain a plurality of test strips 501 of different types. In this way, several types of analysis may be performed from a single housing.

Figure 12:
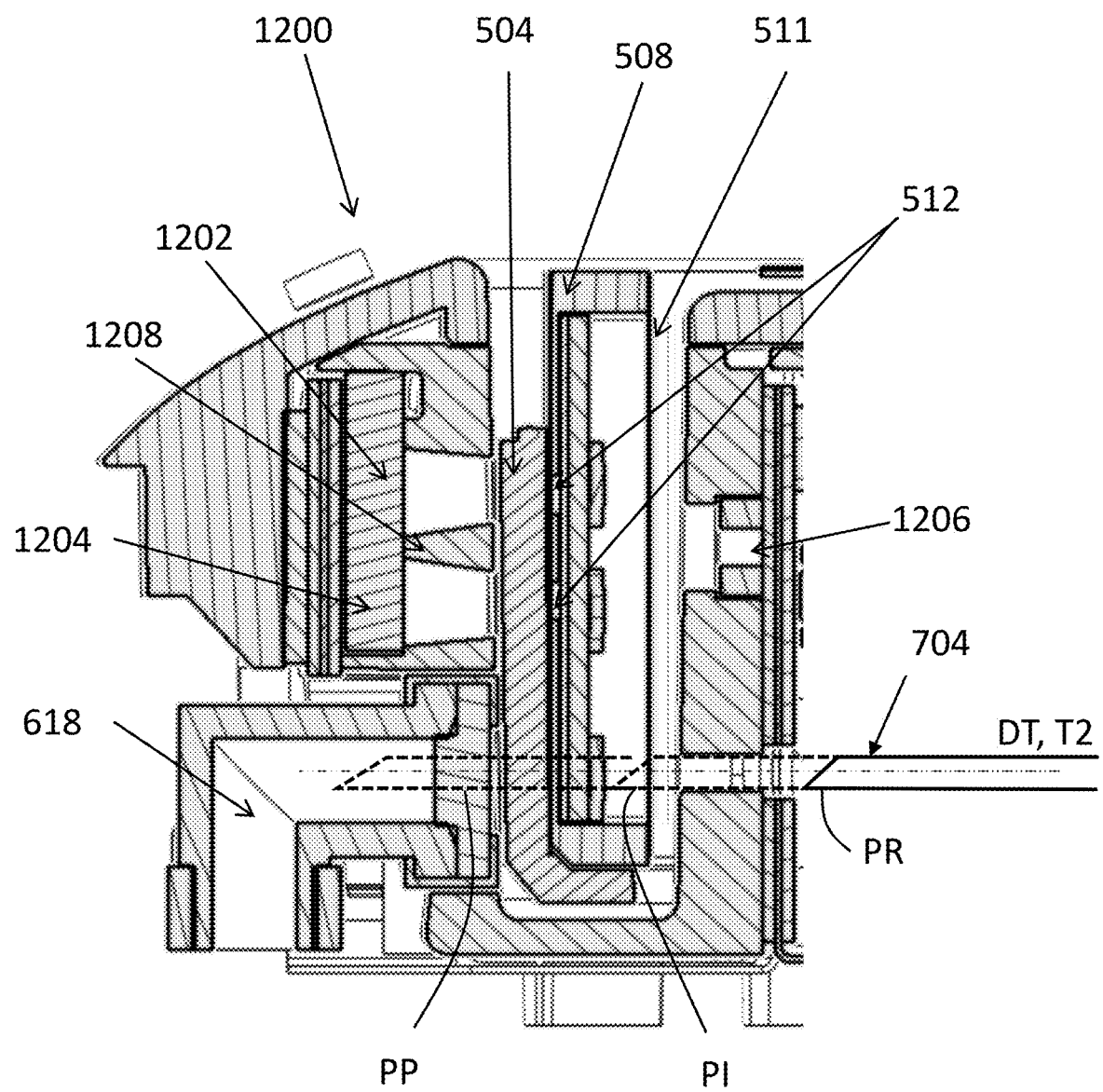
FIG. 12 This figure shows a cross-sectional view, in a plane passing through a radial direction and through the axis of rotation, of the injection zone, the analysis zone and the measurement zone, when the three zones are coinciding.

As previously mentioned, each chamber 510 is covered and closed by a lid (visible in FIG. 12 at reference 511). The lid hermetically isolates test strips 501 received in a chamber 510 from the external environment and from adjacent housings. Chamber 510 becomes accessible for liquid injection, typically by piercing the lid (e.g. by injector 604). So, before an analysis, the test strip reagents are protected from possible contamination. In addition, after an analysis, the lid may contain urine introduced into the chamber 510. The lid may take the form of a continuous film. The film is glued to the outer wall of the rotary support to cover the chambers 510. This configuration makes it easier to position the lid 511 on the rotary support 500. Alternatively, each chamber 510 may be covered by a separate liner. This configuration limits the risk of contamination of test strips received in two adjacent housings. Alternatively, test strips may be individually encapsulated. This configuration is particularly relevant when the test strips are linked together to form a ribbon. In fact, the ribbon may be assembled in the rotary holder without the need for an additional lid. This facilitates assembly of the urine analysis device 100. The lid is made of an inert material. For example, the lid may be made of silicone or acrylic. Preferably, the lid is of medical grade, to avoid contamination of the test strips with undesirable products contained in the lid. Test strip reagents are therefore preserved intact prior to analysis. In addition, the lid is transparent, preferably exceeding 99%. A colorimetric analysis may therefore be performed on a test strip through the lid.

Drive Actuator

The cartridge 202 is, when positioned in station 200, mechanically coupled to a drive actuator 600 (FIGS. 6, 8 and 10), via its mechanical coupler 506 and a complementary mechanical coupler 602 of station 200, to be rotated about axis A. The cartridge 202 may then be selectively positioned to align a test strip facing the injector, referenced 604, or the analyzer, referenced 606. The use of cartridge 202 provides a simple moving assembly with a single axis of rotation. In addition, this configuration reduces the constraints associated with positioning and arranging the injector 604 and analyzer 606 in the test device 100.

The drive actuator 600 may be offset from axis A, and a gear train 608 (which may also act as a reduction gear) drives the complementary mechanical coupling 602. The complementary mechanical coupling 602 of station 200 is located on rotation axis A.

The drive actuator 600 may drive the cartridge 202 in clockwise or anti-clockwise direction. The cartridge may then quickly reach the desired position, following the shortest trajectory. This further reduces the constraints associated with the positioning and arrangement of the injector 604 and the analyzer 100.

The drive actuator 600 is, for example, a drive motor, such as a stepper motor or DC motor. Alternatively, the drive actuator 600 may involve a hydraulic or other system.

Fluidic Circuit

The collection port 218 is fluidly connected to a manifold 610, then a collection pipe 612, then a pump 614, then a delivery pipe 616 and then the injector 604. The injector 604 is movable in the case 204, so that the injector may move to inject urine selectively onto a strip or into a drain pipe 618 connected to the drain port 310, depending on the position of the cartridge 202 in the station 200. The urine collected by collection port 218 is set in motion in the fluidic circuit by pump 614. Delivery pipe 616 may include a flexible portion (not shown in FIG. 6, for example), particularly at the end connecting it to the injector, to accommodate injector movement. Injector 604 typically comprises three positions: a withdrawal position PR, an injection position PI and a purge position PP. In the withdrawal position PR, the injector 604 does not interfere with the rotation of the cartridge 202 in the annular housing 212; in the injection position PI, the injector 604 is able to inject urine onto a strip positioned in the injection zone ZI; in the purge position PP, the injector 604 is connected to the drain pipe 618. Typically, in the withdrawal position PR, the injector 604 is entirely radially internal to the annular housing 212, fully retracted; in the injection position PI, the injector 604 is partially internal to the annular housing 212 and partially in the annular housing 212; in the purge position, the injector 604 is partially internal to the annular housing 212, partially in the annular housing 212 and partially external to the annular housing 212. For the injector to be in the purge position PP, the cartridge 202 must also be in the purge position, i.e. the purge opening 514 of the rotating support 500 must be aligned with the injector 604 (radially aligned with a distal injection end of the injector).

Pump 614 may draw urine. For example, the pump draws in between 5 microliters and 1 mL, preferably around 20 microliters. In addition, the pump may deliver a sufficient volume of urine to injector 604 to enable a conclusive analysis. The suction rate of pump 614 is chosen according to the diameter of the collection orifice. Beneficially, the pump may draw urine from the collection port to the injector without forming air bubbles.

In another phase, after urination and outside the flushing sequence, pump 614 may also draw air from collection port 218 and eject it via discharge port 310. In this way, the pump may expel urine or water from the urine analysis device. Urine collected for analysis is thus protected from possible contamination by toilet water or water from a previous collection. In a further or alternative phase, the pump 614 may be designed to draw in water when the toilet flush is activated, in order to evacuate the urine contained in the urine analysis device.

The pump 614 may be of various types. Pump 614 may be a miniaturized peristaltic pump. Pump 614 may be a miniaturized pneumatic pump system as detailed below. In the case where pump 614 is a miniaturized pneumatic pump, this pneumatic system is configured to create a vacuum to draw urine from collection port 218, and then a positive pressure to push urine towards injector 604 and the purge channel. The pneumatic system pump may be a rotary pump, with the direction of rotation selectively providing negative pressure or positive pressure respectively. The pneumatic system pump may also be a piezoelectric pump.

When urine is aspirated, the injector may be set to purge to release air until urine is pre-loaded.

The solution presented enables precise control of the volume delivered to the urine analysis device.

Curved Injector

In connection with FIGS. 6 to 8, the injector 604 will be described in more detail. The injector 604 comprises a distal end, so-called injection end, 700 and a proximal end, so-called connection end, 702, which is typically configured to be connected to the delivery pipe 616 (in particular the flexible portion of the delivery pipe, which is not shown in FIG. 6, so that the proximal end 702 opens to the open air). Injector 604 may comprise a needle 704, and distal end 700 may then be the end of needle 704.

In order to inject urine onto the strips 501, the injector 604 is translationally movable in a translation direction DT relative to the case 204. A displacement actuator 620 is provided in the case 204 to move the injector. Injector 604 is positioned in the case 204, radially inside annular housing 212. Similarly, the displacement actuator 620 is also positioned radially inside the annular housing 212. However, due to the arrangement of the chambers 510, the acceptable angular position for injection (known as the injection window) is quite small. In the case of the injector described in document PCT/EP2021055302 (in FIG. 20 in particular), the window is constrained by the inclination between a radial direction (along a radius of the circle defined by the chambers) and a depth of the chamber. Consequently, the number of drive motor steps to be activated for the chamber to be correctly positioned during injection is low.

Figure 6:
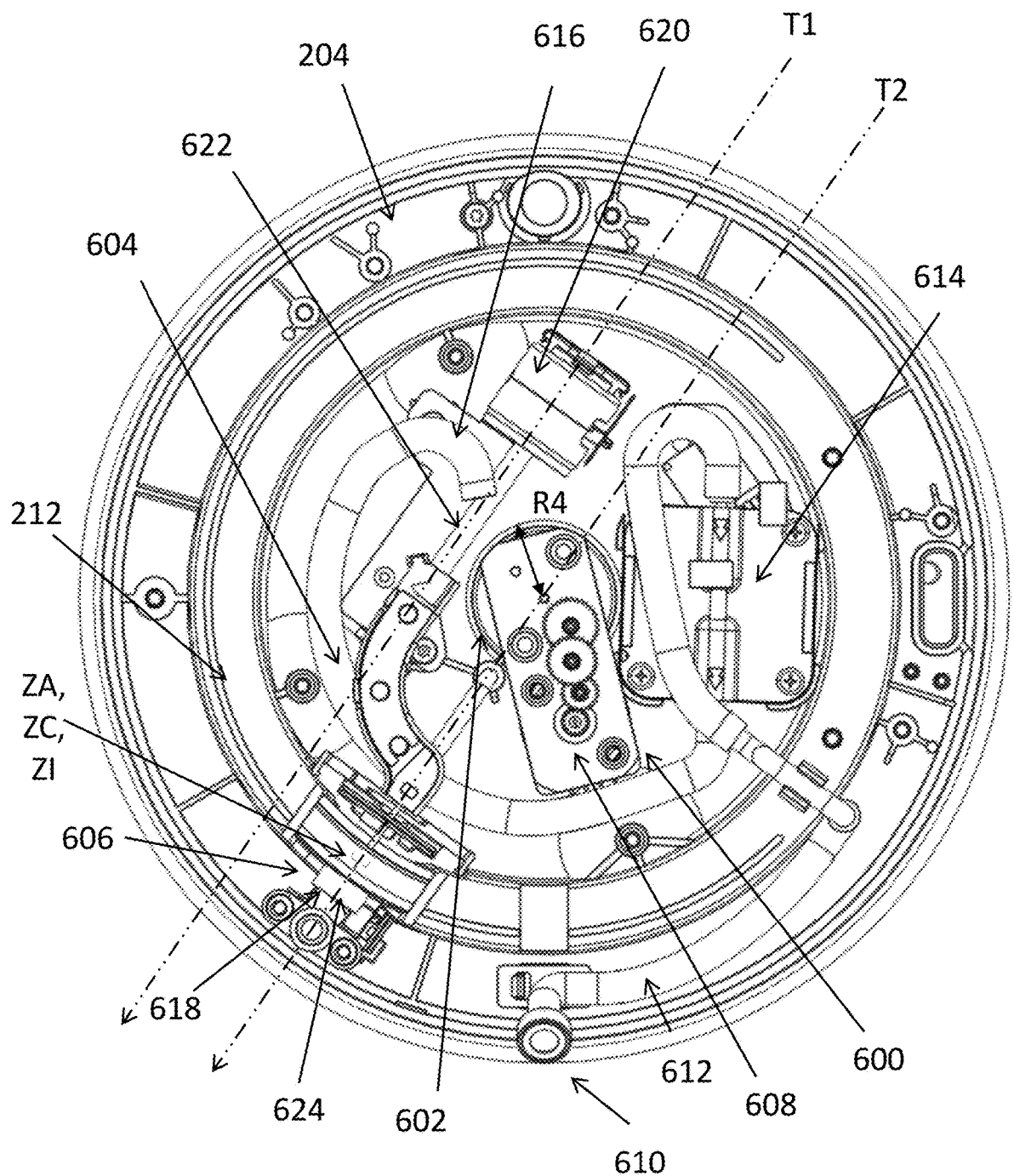
FIG. 6 This figure shows a cross-sectional view of the station in the plane orthogonal to the axis of rotation.
Figure 7:
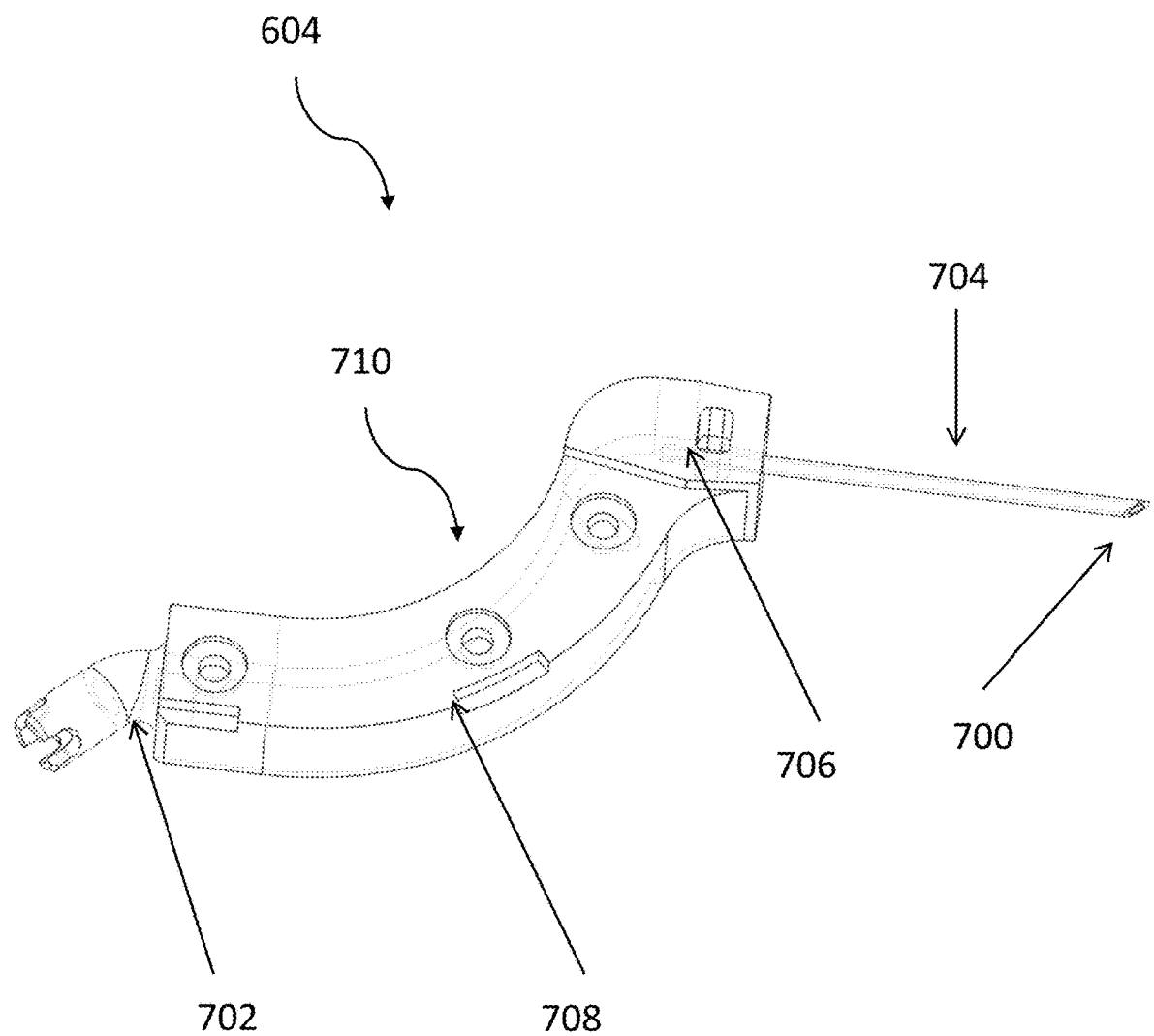
FIG. 7 This figure shows an isolated three-dimensional view of the injector.
Figure 8:
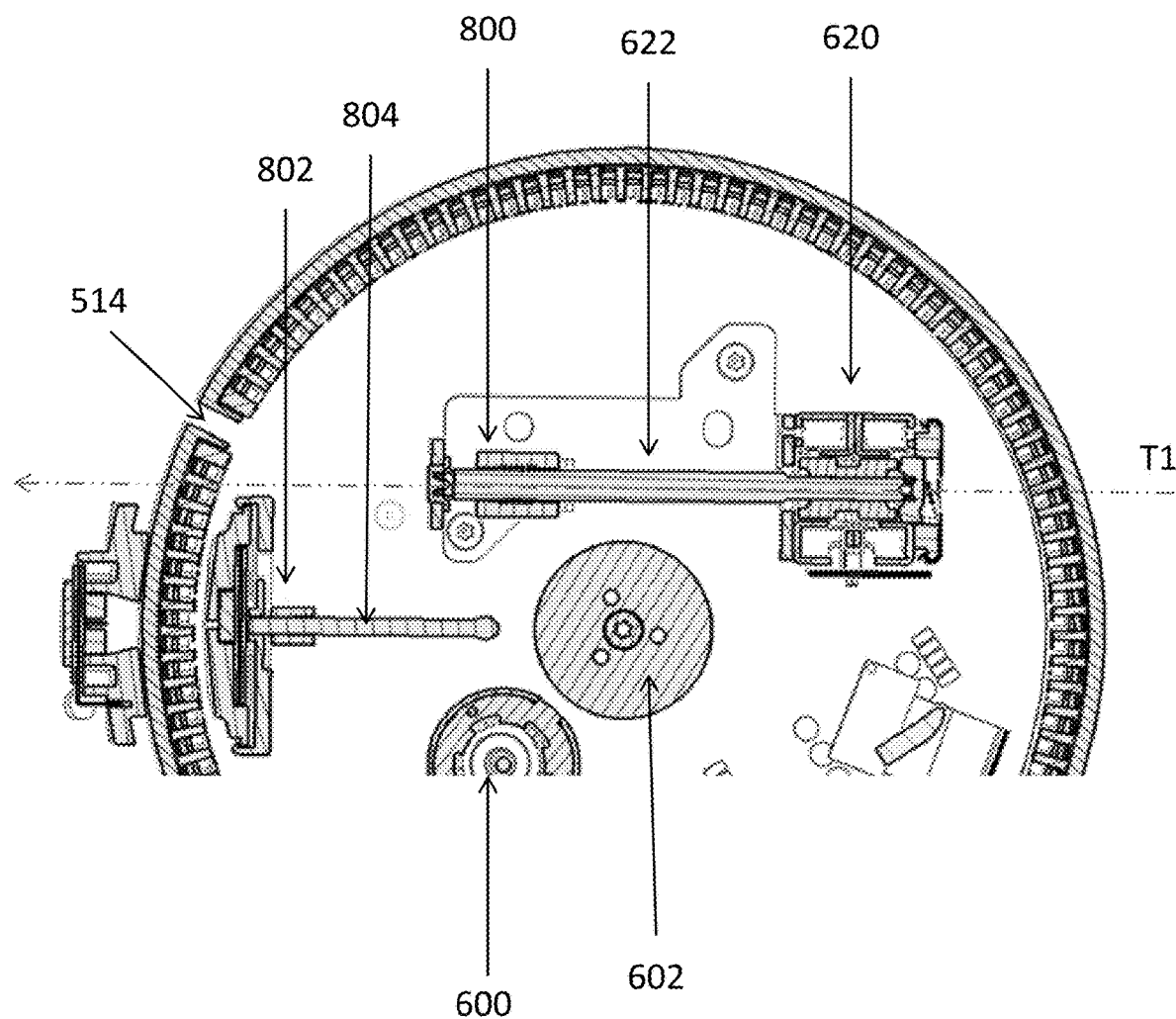
FIG. 8 This figure shows a cross-sectional view of the analysis device in a plane orthogonal to the axis of rotation.

The injector 604 shown in FIGS. 6 to 8, does not present these difficulties. In one aspect, injector 604 has a curved shape, so that the axis of translation at which injector 604 is translated is offset from the axis of translation of the distal end 700. In the embodiment shown in FIGS. 6 to 8, it is understood that a portion of the injector which channels the fluid is curved (and that the fluid path substantially follows this curve). In particular, if we define a first axis T1, which is the axis at which the injector 604 receives the translational movement, and a second axis T2, which is that of the displacement of the distal end 700, these two axes T1, T2 are not coinciding when seen from above or below (along the axis of rotation A) or when projected in a plane orthogonal to the axis of rotation A. This allows the displacement actuator 620 to be relocated to a less cluttered area of the case 204. The second axis T2 is parallel to the translation direction DT.

According to an aspect, the injector 604 may also be defined by the offset in the plane orthogonal to axis A between the distal end 700 and the proximal end 702 of the injector. This offset is obtained in particular by a curved shape of the injector 604.

According to one aspect, the injector 604 may also be defined by the fact that it is located radially inside the annular housing 212 and that the distal end 700 moves in translation in a radial direction or substantially in a radial direction (i.e. radial to within a few degrees, for example 10°, preferably 5° and even 2° on either side of the radial direction, or even 1°). This radial displacement is made possible by the curved shape (projected in a plane orthogonal to the axis of rotation A) of injector 604.

The curved shape of the injector 604 makes it possible to bypass the mechanical coupler 602 located at the axis of rotation A, while having the second axis T2 coincide with a radius of the circle defined by the chambers. In other words, the distal end 700 moves along a radial direction, and therefore orthogonal to the lid 511, the strip 501 and/or the bottom of the chambers 510. Consequently, the first axis T1 does not pass through the mechanical coupling 602, but the second axis T2 passes through the mechanical coupling 602. In this way, injector 604 does not interfere with a cylinder of radius R4 centered on axis A. This leaves an axial space where the hub of the cartridge support 500 is housed.

The first axis T1 is offset from axis T2 (in a plane orthogonal to the axis of rotation) by an offset distance equal to minus the radius distance R4 (R4 plus the thickness of a cover, plus at least one functional clearance). Radius R4 may be at least 3 mm. R4 may be at least 5 mm. The offset distance is typically between 5 and 15 mm, or even between 5 and 10 mm.

The second axis T2 is advantageously radial or substantially radial (plus or minus 2°, or even 5°, or even 10° on either side of a radial direction).

The curvature of injector 604 may comprise two successive inverted bends 706, 708 (see FIG. 7 in particular). In particular, between distal end 700 and proximal end 702, injector 604 comprises an intermediate portion 710. The two bends 706, 708 may be formed in the intermediate portion 710. Both bends 706, 708 are rounded, to minimize disruption to fluid flow. The proximal bend 708 (closest to the proximal end 702) may have a complementary shape to the mechanical coupler 602 of station 200 to allow the distal end 700 to have maximum translational amplitude. To this end, the distal bend 706 (closest to the distal end 700) may have a smaller radius of curvature, so that the intermediate portion is predominantly formed by the proximal bend 708. The essential function of the distal bend 708 is therefore to enable the injector 604 to be inserted into the case 204, bypassing the mechanical coupler 602, and the function of the proximal bend 706 is to realign the injector 604 (in particular to realign the needle 704) in a radial or substantially radial direction.

In one variant, the needle itself is curved.

In an embodiment, injector 604 is rigid. By rigid, it is meant that it does not deform during normal use of the device. In particular, the intermediate portion 710 is rigid.

In the withdrawal position PR, injector 604 may be less than 2 mm from mechanical coupler 602 (closest distance).

In the purge position PP, the distal end 700 of injector 604 is radially external to annular housing 212. The purge opening 514 may also be used as a zero marker for obtaining the position of cartridge 202.

In an embodiment, the curvature of the injector 604 is only in a plane orthogonal to the axis of rotation A. In another embodiment, the injector may have a curvature that creates an offset along the axis of rotation A, so that the distal end 700 is higher or lower (along the axis of rotation A) than the proximal end 702. This makes it possible to manage level differences in the device 100.

Several options are available for moving the injector 604 in translation. The displacement actuator 620, mounted in the case 204, is designed to generate the movement. FIG. 8 illustrates a screw-nut connection. The displacement actuator 620 may be a displacement motor 620, for example an electric motor, which drives a rod 622 in rotation. The rod 622 cooperates mechanically with a nut 800 integral with the injector 604, so that the rotational movement of the rod about the first axis T1 is transformed into translation of the nut 800 at the first axis T1. Stem 622 and nut 800 each comprise a thread which cooperates with each other. As a result of the curvature of the injector 604, the bulkiness of the displacement actuator 620, the rod 622 and the other components enabling a functional injector to be produced are offset in a free zone of the case 204, next to the mechanical coupler 602 of the station 200, while the proximal end 700 of the injector 604 may move along the second axis T2, which is a radial or substantially radial direction. The nut 800 is referred to as a captive nut, in the sense that it cannot rotate on itself.

The screw-nut connection ensures good conversion of movements, with no step jumps, offset between setpoint and result, or even loss of connection in the event of the station 200 falling. What's more, given the masses of the components, friction and the need for lubrication are low. For example, lubrication during assembly is sufficient.

Nut 800 may be produced as a threaded insert or by tapping a hole.

Alternatively, the displacement actuator 620 may be a linear motor, or even a linear actuator (cylinder, etc.), which produces translational movement directly.

To improve precision, the injector 604 may be integral with a guide 802 (or slide) in translation at the level of the first axis T1. Guide 802 may comprise a circular orifice which cooperates with a fixed rod 804 integral with case 204. When the guide 802 is in the form of a circular hole, it cannot become detached from the fixed rod 804, which ensures good robustness (e.g. in the event of the station 200 falling).

Figure 9:
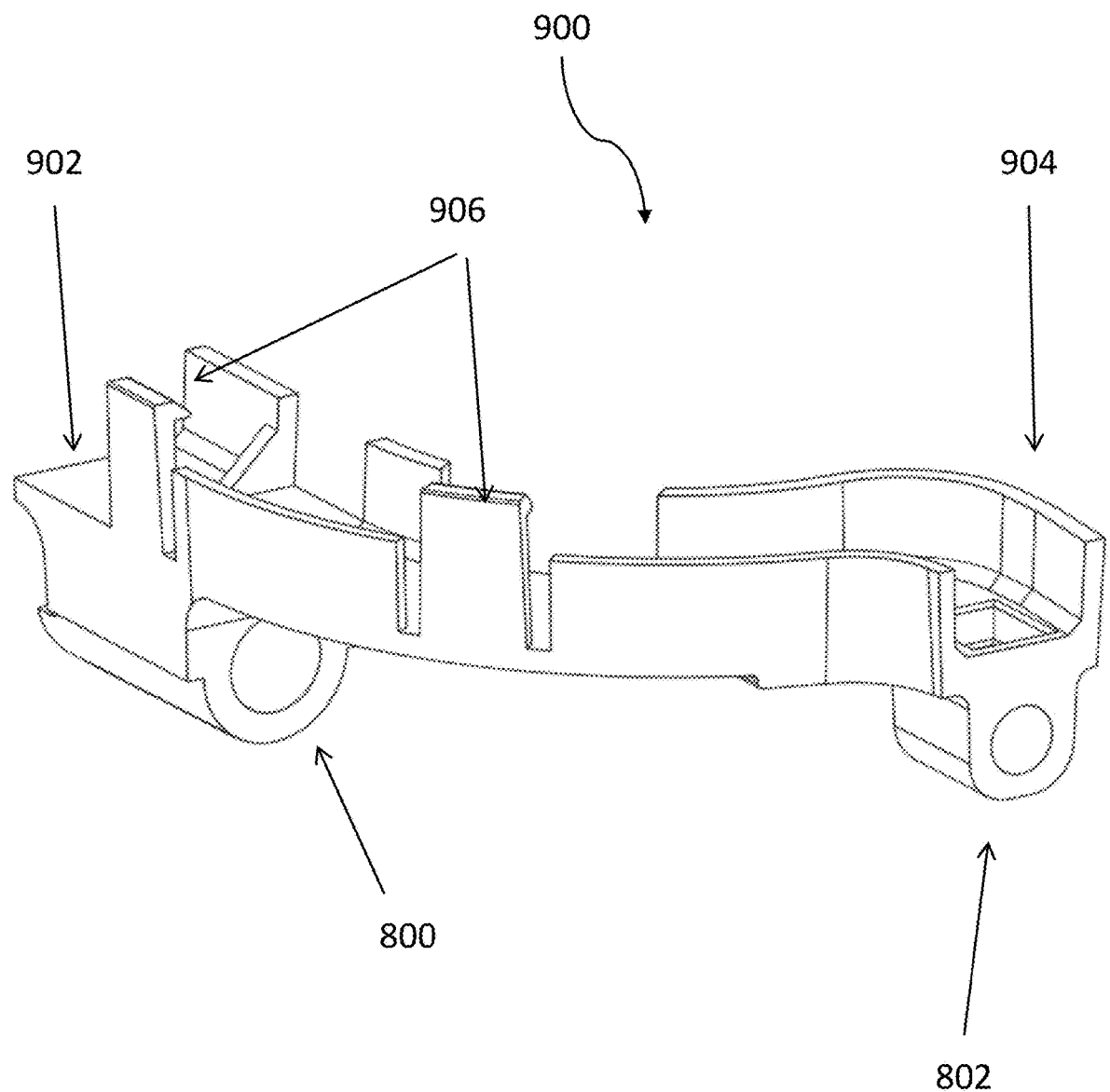
FIG. 9 This figure shows an isolated three-dimensional view of the carriage carrying the injector.
Figure 10:
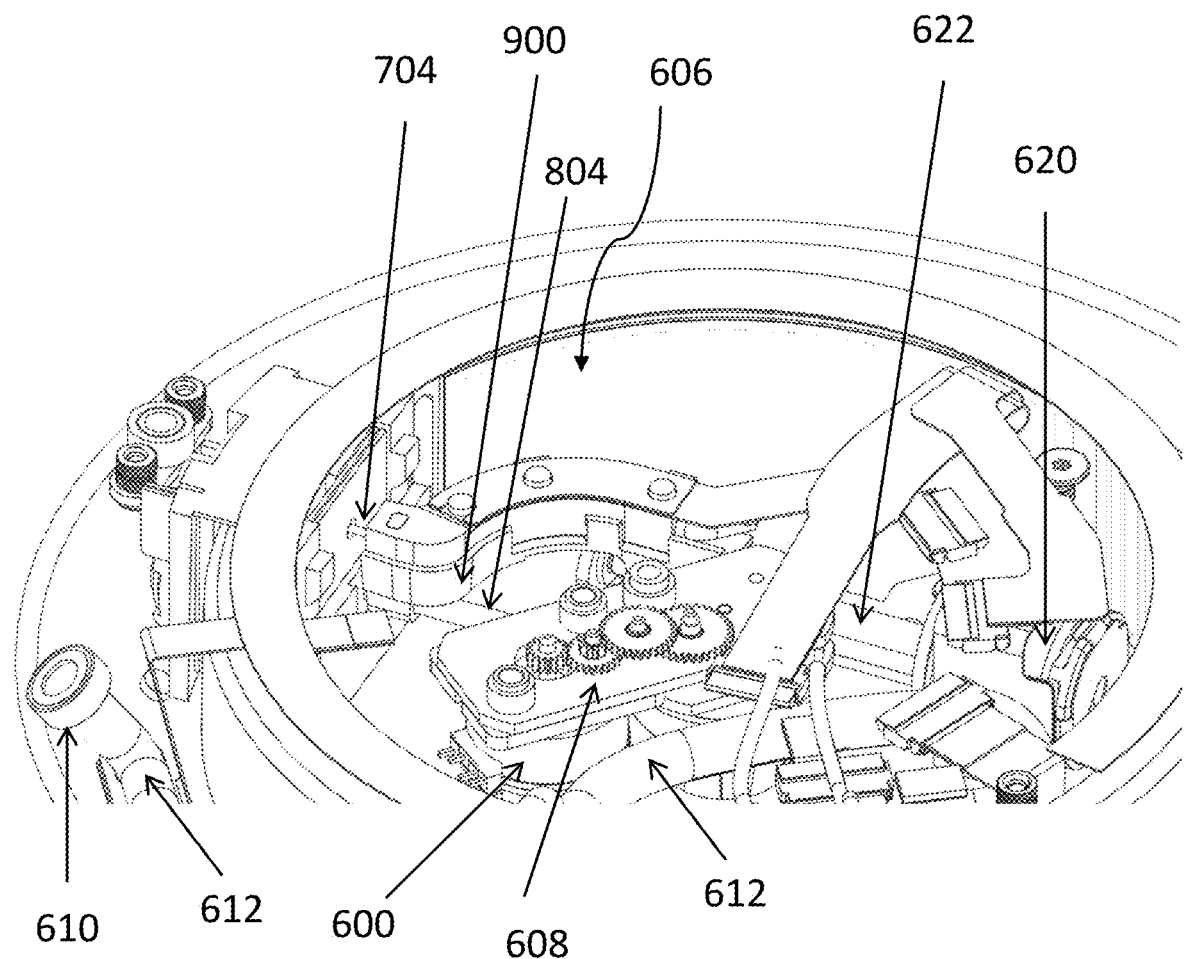
FIG. 10 This figure shows a partial three-dimensional view of the station.

Injector 604 may be mounted on a carriage 900, shown on its own in FIG. 9 and visible in the case in FIG. 10. Carriage 900 has a curved shape that may accommodate injector 604. The force of the displacement actuator 620 may be transferred to the carriage 900 rather than directly to the injector 604, to protect the latter from any mechanical stress. Indeed, the offset caused by the curvature of injector 604 and the reaction force of lid 511 when pierced by injector 604 may create a parasitic torque. The carriage 900 provides additional strength to the system. For example, at a proximal end 902 of carriage 900 is the nut 800, which couples with rod 622. At a distal end 904 is the guide 802, in the form of a circular orifice. The offset between the two orifices of nut 800 and guide 802 may correspond to the offset between first translation axis T1 and second translation axis T2 (in a plane orthogonal to rotation axis A). Carriage 900 may include retaining clips 906 to hold injector 604 in position.

Displacement actuator 620 moves injector 604 into the three positions mentioned above: withdrawal position PR, injection position PI, purge position PP. When the displacement actuator 620 is activated, these movements are performed between the three positions PPI, PI, PP.

Other types of motor and/or mechanical linkage allow the injector 604 to be moved in translation.

The distal end 700 may also be configured to pierce the lid 511 of cartridge 202. A bevel may be provided to facilitate insertion.

Needle 704 may have a diameter of around 0.5 mm. The proximal end 702 and the intermediate portion 710 may be one-piece (e.g. made by 3D printing), and the needle 704 is inserted into the intermediate portion, which comprises a hole provided for this purpose. Needle 704 may be made of metal.

The injection zone ZI, which corresponds to the angular window or sector (around the axis of rotation) for positioning a strip 501 for a satisfying injection of urine by the injector 604, typically comprises a few degrees maximum (less than 5°, or even less than 2°). In the case of a stepper drive actuator (in the form of a stepper drive motor 600 for example), this injection window corresponds to a few steps (the number depending on the drive motor 600 itself and the gear train 608).

Injector 604 may inject a controlled volume of urine onto a test strip, for example between 2.5 microliters and 3.5 microliters. The injector injects a sufficient volume of urine onto a test strip to perform a conclusive analysis without the risk of urine overflowing the chamber.

Injector 604 may inject a controlled volume of urine onto test strip 56 in two stages. For example, injector 604 may inject between 2.5 microliters and 3.5 microliters twice. This solution takes into account the reaction and migration time of the urine on test strip 501.

Position Sensor and Injector

A position sensor 624 may be provided in case 204 to obtain the position of cartridge 202 and/or strips 501 relative to case 204, and more precisely relative to injector 604 and/or analyzer 1200. This improves accuracy, since the displacement actuator 620 may be controlled by position setpoints using data from the position sensor 624 (feedback loop).

In order for the injector 604 to inject urine correctly onto the selected strip 501, it is important to know the position of the strips 501 in the annular housing 212. In particular, due to the structure of the cartridge 202, assembly inaccuracies are possible, so that the strips 501 are not regularly positioned (slight offsets, but in view of the distances involved, which may generate incorrect analyses).

Figure 11:
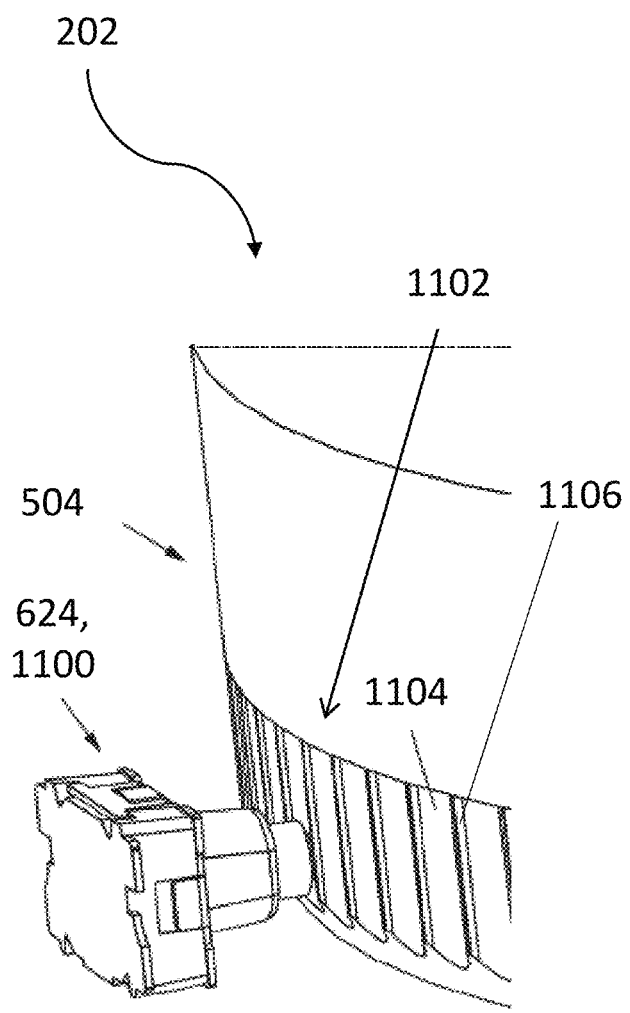
FIG. 11 This figure shows a three-dimensional view of another position sensor design.

In an embodiment, the analysis station 200 therefore comprises a position sensor 624 (visible in FIG. 6 or 11). For reasons of bulkiness, the position sensor 624 may be positioned at least partially, in the case 204, radially outside the annular housing 212. Position sensor 624 is able to identify the position of a marker on cartridge 202 when the marker is within control zone ZC. Typically, there are at least as many markers as there are strips 501, so that each strip 501 may be identified by a marker. As previously indicated, the injector 604 is configured to inject urine in an injection zone ZI of the annular housing 212 and the position sensor 624 is configured to obtain the position of a marker associated with the strip 501 in a control zone ZC of the annular housing 212.

In an embodiment, the injection zone ZI and the control zone ZC are coinciding or in close proximity. In other words, the position sensor 624 is able to measure the position of a marker associated with a strip 501 when the marker is positioned in the injection zone ZI or in a proximity zone of the injection zone ZI (the measurement is made on this marker, and not by deduction from a measurement on a marker outside or at a distance from the injection zone ZI). This means that the position sensor 624 makes it possible to precisely know the position of a strip of interest 501 in the injection zone ZI and therefore to inject urine correctly onto the strip of interest 501. Inaccuracies in the position of strips 501, due to the positioning of the strips in the separator 508 and the separator 508 itself in the cartridge 202 (which is flexible), are generally small from one chamber to the next. Consequently, by measuring the position of a marker in a proximity zone of the injection zone ZI, and therefore close to the strip 501 of interest, we obtain fairly accurate data on the position of the strip 501 of interest in this injection zone ZI. By proximity zone, it is understood less than 30° on either side of the injection zone, or even less than 20°, or even less than 10°, or even less than 5°. The closer the position sensor 624 measures a marker to the strip 501, the better the accuracy for this strip 501. Conversely, the further the position sensor 624 measures the position of a marker away from the injection zone ZI, the more positioning inaccuracies may accumulate, so that the strip of interest may not actually be correctly located in the injection zone ZI.

In an embodiment, the marker is the strip 501 directly, which maximizes accuracy. A more detailed description is given below. Alternatively, the marker is a markable element located on the cylindrical portion 504 of the cartridge 202 or on the separator 508.

For example, as shown in FIG. 11, position sensor 624 is a mechanical sensor, for example in the form of a tracker 1100, mounted in case 204, which cooperates with a lobed cam 1102 of cartridge 202 (of cylindrical portion 504 for example). The marker is then the top 1104 or bottom 1106 of the lobed cam that is closest to a strip. Thus, by measuring the position of the marker, which is close to the strip, the position of the strip may be known, and the latter may be correctly positioned in the injection zone ZI.

For example, position sensor 624 may comprise an electromagnetic sensor, such as a Hall-effect sensor, and the marker may be a magnetic element on the cartridge. A magnetic element may be mounted on the rotary support facing or immediately adjacent to each chamber 510.

In an embodiment, position sensor 624 is radially aligned (when projected in a plane orthogonal to the axis of rotation) with the distal end of the injector (i.e. same angular location around axis of rotation A), but offset along the axis of rotation. In this way, the measurement obtained is relevant to the injection.

In an embodiment, position sensor 624 is an optical sensor that locates the marker by analyzing a received light signal. More specifically, position sensor 624 may be the analyzer 606 itself. This makes for greater compactness and accuracy, since the marker is very close to the strip (or is even the strip).

Analysis and Injection

FIG. 12 illustrates in detail an embodiment of analyzer 606, referenced 1200 here. Analyzer 606 may perform colorimetric analysis on test strips. By "colorimetric analysis" it is understood absorbance or fluorescence measurement under predetermined illumination, in transmission or reflection. The analyzer 606 may then determine one or more analysis results.

The analyzer 606 may be an optical analyzer 1200, comprising at least one light source 1202 (e.g. one or more light-emitting diodes), 1204 and a sensor 1206 (e.g. a CCD ("Charged Coupled Device") or CMOS ("Complementary Metal Oxide Semiconductor") photodiode. The light source may comprise two separate sources 1202, 1204 (e.g. two different wavelengths).

The analyzer 1200 is typically located on either side of the annular housing 212, so that the light emitted by the light source 1202, 1204 may pass through the transparent cylindrical portion 504, then the orifices 512 of the separator, then the strip, to finally reach the optical sensor 1206. An optical splitter 1208 guides the two light sources 1202, 1204 to prevent light leaking from one optical path to the other.

As previously mentioned, the analyzer 1200 operates in the analysis zone ZA.

In an embodiment, the analyzer 1200 features several LEDs with wavelengths specific to the different reagents contained in different types of test strips. In this way, the urine analysis device may perform different analyses with precision.

For example, each light source 1202, 1204 may each comprise a white LED and an ultraviolet LED. A vertical separator (not visible in FIG. 12) may be provided to prevent activation of the white LED from exciting the ultraviolet LED.

Alternatively, the analyzer 1200 may comprise a single LED. For example, the LED may be white. In this case, the LED may cover the entire visible spectrum. This configuration reduces the complexity of the analyzer.

The analyzer 1200 may also include a collimator. The collimator is used to direct the illumination of the LED(s) onto the test strip.

Sensor 1208 may measure the absorbance or fluorescence of the test strip reagent, notably by transmission or reflection, to establish the analysis result(s).

The sensor 1208 may be fitted with a filter. The filter increases the sensitivity of the optical sensor to specific wavelengths. The result is highly accurate analysis.

As illustrated in FIG. 12, the analyzer 1200 is arranged on either side of the annular housing 212 (and therefore on either side of the cylindrical portion 504 when the cartridge 202 is inserted in the station). A first part of analyzer 1200 (e.g. light source 1202, 1204) is radially external to annular housing 212 and a second part of analyzer 1200 (e.g. optical sensor 1206) is radially internal to annular housing 212. The analyzer 1200 operates by transmitting light from the first part to the second part.

The first part comprises the light source 1202, 1204, for example in the form of a pair of LEDs 1202, 1204. When aligned, light is guided through holes 512 to illuminate test strips 501. A first LED 1202 of the pair may be white in color to cover the entire visible spectrum and determine color changes of the test strip 501. A second LED 1204 of the pair may be monochromatic, for example ultraviolet, to excite fluorophores and enable observation of their emission wavelength.

The second part comprises the optical sensor 1206. The optical sensor 1206 is of the spectral type. It comprises several photodiodes topped by filters for measuring light intensity at different wavelengths in the visible spectrum. The sensor 1206 is compatible with absorbance and fluorescence optical measurements.

Sensor 1206 may be used for different types of test strips. For example, test strip 501 is of the immuno-chromatographic type and comprises a test zone and a control zone aligned respectively with ports 512, the color change of which provides a result. In another example, test strip 501 may be a colorimetric strip and comprise two separate test zones (for simultaneous testing of urine pH and specific gravity, for example) aligned respectively with ports 512.

Alternatively, the analyzer 1200 may be mounted on a linear motor. In this way, the analyzer may be brought closer to a test strip for more precise analysis.

In an embodiment, the analysis zone ZA of analyzer 1200 is coinciding with the injection zone ZI of injector 604. In other words, drive actuator 600 does not need to be activated and to rotate cartridge 202 between urine injection by injector 604 and analysis of strip 501 by analyzer 1200. Injector 604 and analyzer 606, 1200 are arranged to work angularly at the same place and may interact with the same strip (without rotating cartridge 202). There are many advantages to this. One interest is kinematics: analysis may start just before (e.g. at most two seconds or at most one second), at the same time or just after injection, so that the kinetics of the chemical reaction (e.g. speed of color change) of the strip 501 once in contact with the urine may be observed. Another advantage is precision: a good position for injection means a good position for analysis. In terms of size, as shown in FIG. 12, the optical sensor 1206 may be offset along the axis of rotation A from the injector 604 (in particular needle 704). In this way, it is possible to obtain a configuration that allows the same strip to be injected and analyzed without rotating the cartridge (and therefore without activating the drive actuator 600).

In an embodiment, the analysis zone ZA of the analyzer 1200 is coinciding with the control zone ZC of the position sensor 624. This ensures that the strip 501 is correctly positioned for measurement by the analyzer 1200, and thus provides a quality measurement. In particular, the optical sensor 624 may be the analyzer 1200 itself.

In an embodiment, the analysis zone ZA, injection zone ZI and control zone ZC are coinciding. This means that the position sensor 624 determines that a strip 501 is correctly positioned by means of a marker located in a zone close to the strip 501. Injection and analysis then take place without the cartridge 202 being rotated.

Direct Measurement of the Position of the Test Support (e.g. Test Strip).

In an embodiment already mentioned above, the marker for the position sensor 624 is the strip itself. In this way, position sensor 624 is configured to directly measure the position of a strip relative to case 204. This avoids uncertainties in positioning the strip in the separator or uncertainties in the position of the separator 508 in the rotating support 500.

Figure 13:
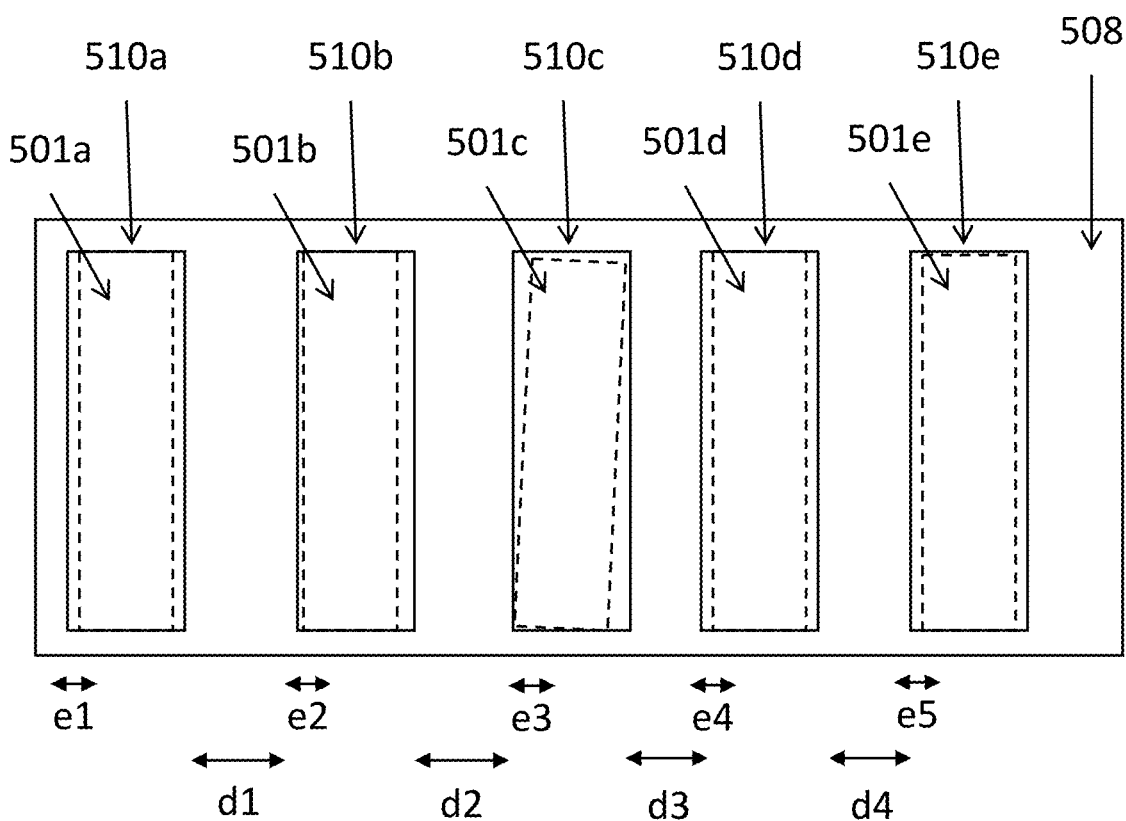
FIG. 13 This figure shows a flattened schematic view of a separator with chambers and strips, to illustrate irregularities.

FIG. 13 schematically illustrates examples of inaccuracies, using a partial view of a separator 508 shown flat and not wound on the rotating support. Five chambers 510a, 510b, 510c, 510d, 510e are shown, with a respective strip 501a, 501b, 501c, 501d, 501e. Due to the flexibility of the separator 508, the distance d1, d2, d3, d4 between two chambers may vary during installation. Due to the flexibility of the strips and their insertion into the chambers, the position e1, e2, e3, e4, e5 of the strips in their chambers may also vary. It is therefore understandable that a marker positioned on the rotating support 500 cannot take these irregularities into account, and therefore only gives the position of the strip with which it is associated with the extent of these irregularities. The position sensor 624, when directly measuring the position of the strip, completely eliminates these irregularities.

In particular, position sensor 624 is an optical sensor, with no contact with cartridge 202. In FIG. 12, the position sensor 624 is the analyzer 1200 itself (the control zone ZC and the analysis zone ZA are therefore coinciding). This makes for greater compactness and accuracy, as already mentioned.

When the cartridge 202 is rotating and the strips 501 pass in front of the position sensor 624, the position sensor 624 (which may be the analyzer 1200 itself, as previously indicated) receives a light variation corresponding to light passing through the orifices 512 of the separator 508 and on either side of the strip 501, or passing through the strip 501. As a result, the signal detected depends directly on the position of the strip 501 in the annular housing 212, independently of the position of the strip 501 relative to the separator 508 or the rotary support 500. Drive motor 600 may be controlled independently of the position of the rotary support 500 or the separator 508.

A process using this feature will be described below.

Obtaining data directly from the strip also enables the strips to be characterized. For example, depending on their nature, strips may have different extremums. Using the value of the extremum and a table stored in the station, it is therefore possible for the station to know the nature of the strip present in the control zone (and therefore in the injection zone and the analysis zone).

Supplements

As mentioned above, in an embodiment, position sensor 624 is used to determine whether a strip is in the control zone (local position), but not to directly determine the absolute position of the strip in the cartridge (in other words, which strip in the cartridge is in control zone ZC). To do this, the ECU may count the number of strips passing from zero (zero being the through-hole 514, which is easily identified by a higher signal value than the others—as light only passes through air or transparent or nearly transparent components). By coupling the count with a table stored in the ECU's memory, the station may identify the strip. The table may match, for a given cartridge model, the nature of the strip and a strip number (the numbering being unique in each cartridge). Identifier 516 enables station 200 to obtain the cartridge model and therefore to know which table to use.

In an embodiment, the device 100 comprises a urine presence sensor. The urine presence sensor may be in the vicinity of the collection port. The urine presence sensor may then detect when urine is present in the vicinity of the collection port. The urine presence sensor may be a temperature sensor, such as a thermistor. The temperature sensor may be used to distinguish between urine and toilet water. The temperature sensor may also be used to measure urine temperature. In particular, urine temperature may be used to detect periods of fertility, by comparison with one or more reference curves. The use of a temperature sensor reduces the number of components used by the test assembly to perform an analysis. This reduces the complexity and cost of manufacturing the urine analysis device. Alternatively, the urine presence sensor may be any type of liquid detector, such as a capacitive or resistive sensor.

Figure 14:
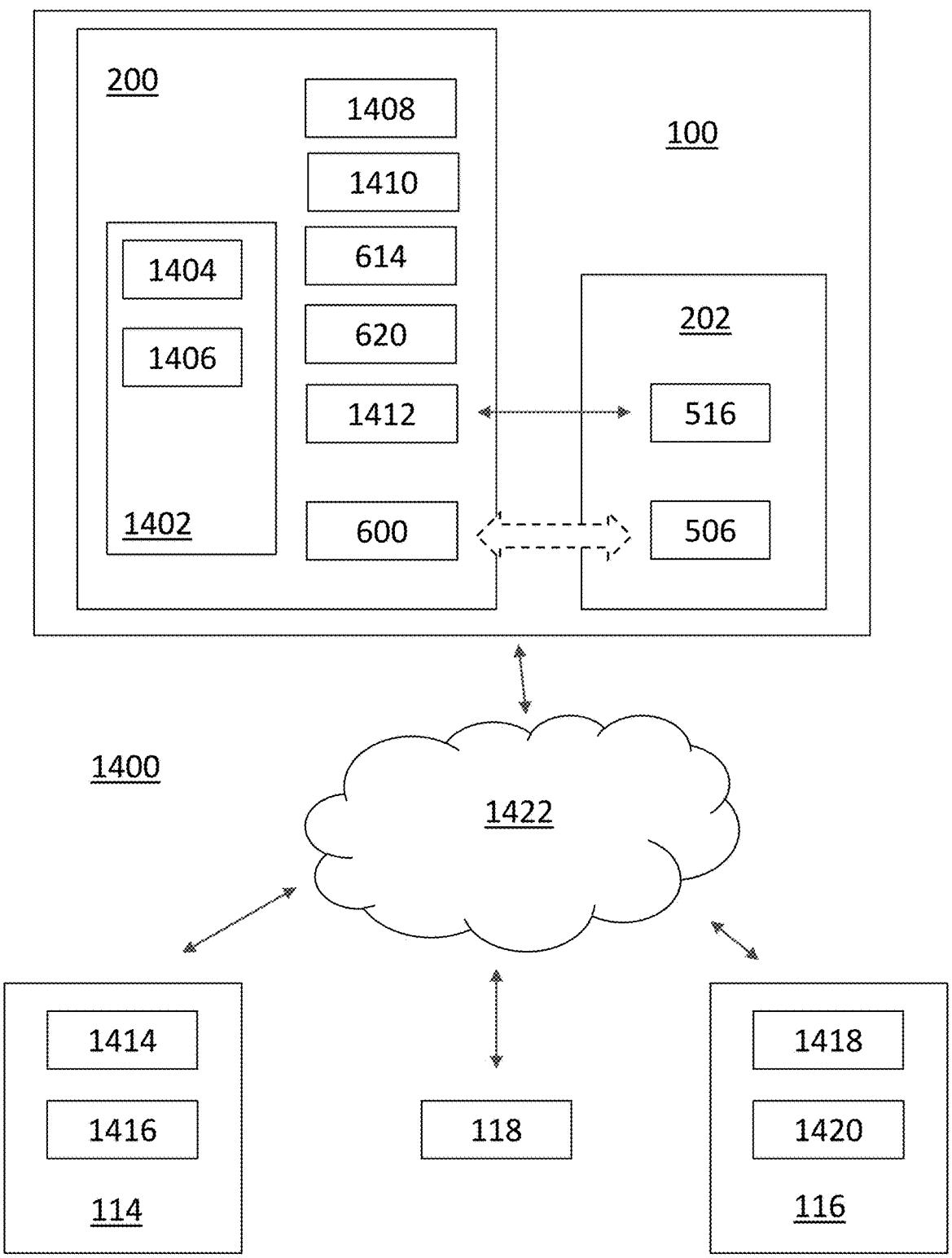
FIG. 14 This figure shows a schematic view of some components of the urine analysis device and its environment.

FIG. 14 shows a schematic view of an analysis environment 1400 comprising the urine analysis device and its surroundings. The station 200 is controlled by an electronic control unit ECU 1402. The ECU 1402 is located inside case 204. The ECU 1402 controls the components of the test assembly to perform a urine analysis using test strips 501 and obtain one or more analysis results. In particular, ECU

1402 manages drive actuator 600, displacement actuator 620, position sensor 624, analyzer 1200 and pump 614.

ECU 1402 typically comprises a processor 1404 and a memory 1406 capable of storing instructions that processor 1404 executes. In particular, the processes described in the description are stored in the form of instruction lines in memory 1406. In order to be able to communicate directly or indirectly with the mobile terminal 114, the server 116 and/or, where applicable, the external activator 118, the station 200 comprises a communication module 1408, typically wireless, for example Bluetooth, WiFi and/or cellular (GSM, 3G, 4G, 5G, 4G-LTE). A battery 1410 supplies power to the various components of station 200. To identify the cartridge 202 in station 200 (via identifier 516), station 200 may include a reader 1412, for example a contactless proximity reader, such as an RFID reader.

In particular, the mobile terminal 114 comprises a processor 1414 and a memory 1416, which are used, for example, to run an application that serves as a user interface for the device 100. The server 116 also includes a processor 1418 and a memory 1420, for processing and storing data generated in particular by the device 100.

The device 100, the mobile terminal 114 and the server 116 communicate with each other via a telecommunication network 1422. Telecommunication network 1422 may be hybrid, comprising a WiFi or Bluetooth network and a cellular network, the roles of which have been explained above.

Control Process

In connection with the urine analysis device 100 described above, various procedures will now be described. The steps described may all be implemented during an analysis or only some of them may be implemented. In particular, these steps are executable from instructions stored in the memory 1305 of the ECU 1402.

Figure 15:
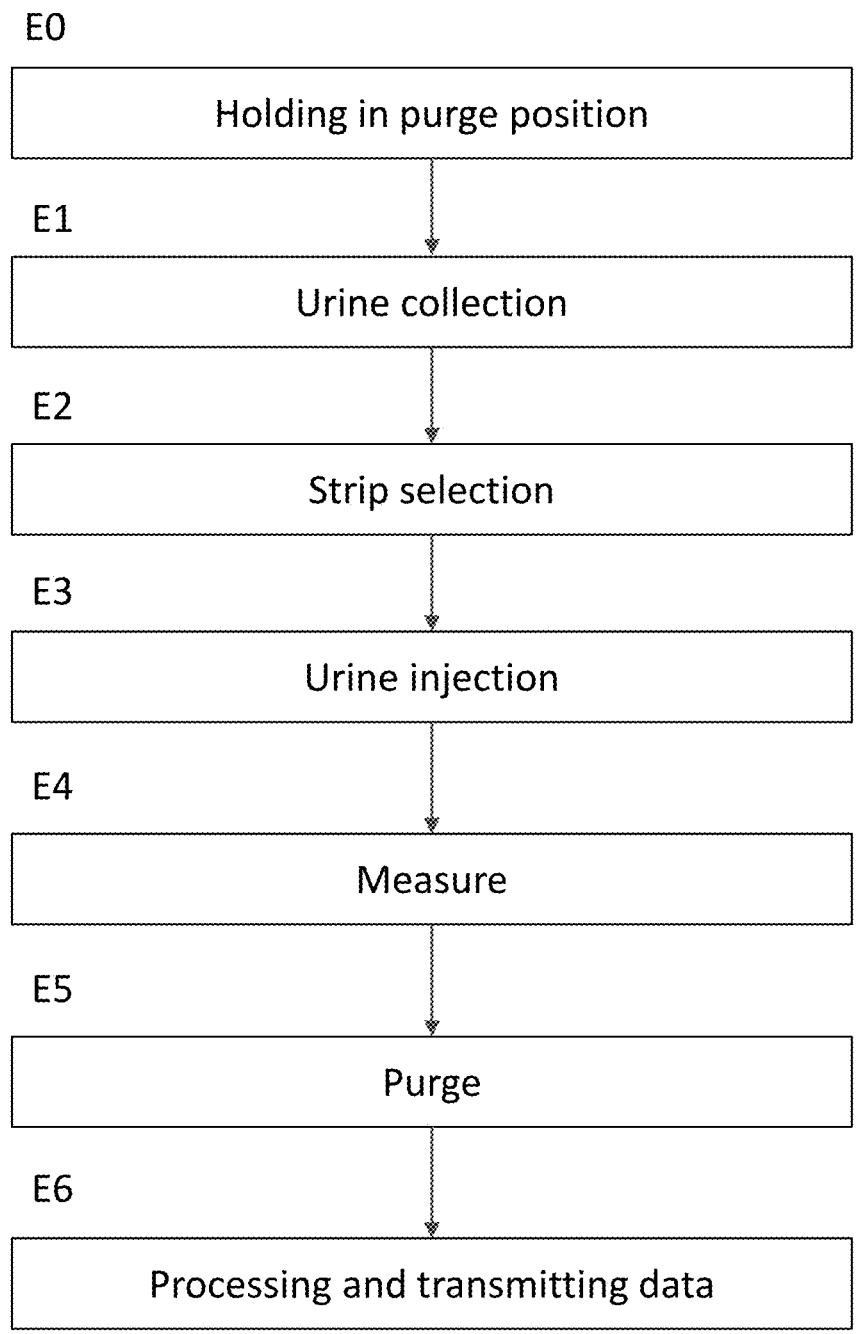
FIG. 15 This figure shows the steps involved in using the urine analysis device.

An overall operating procedure for the 100 device will be described in relation to FIG. 15.

Step E0 consists of holding the urine analysis device 100 in a purge position. The ECU controls drive actuator 600 to bring purge opening 514 of cartridge 202 into injection zone ZI (i.e. aligned with injector 604). To this end, the ECU uses position data obtained by position sensor 624, which may locate opening 512 (e.g. by a stronger light signal, as there is no strip between the light source and the photodiode). Before rotating the cartridge, the ECU has driven the displacement actuator 620 to move the injector to the withdrawal position PR. Once the purge opening 514 is facing the injector, the ECU drives the displacement actuator 620 to move the injector 604 to the purge position PP. This allows the device 100 to be flushed of water or urine residue. In this way, urine or water received from the toilet in the collection pipe 612 may reach the drain port 310.

In step E1 ("urine collection"), the ECU activates pump 614 to convey urine from collection port 218 to injector 604. Injector 604 is still in the purge position PP, and urine may exit through the drain port. This step allows to clean and ensure that the injector is filled with urine. Step E1 may also include a pre-loading step, to bring a controlled quantity of urine to the distal end 700 of injector 604.

Step E2 ("strip selection") involves positioning the urine analysis device 100 in a selection position, with the desired strip 501 facing the injector 604. The ECU activates displacement actuator 620 to move injector 604 from purge position PP to withdrawal position PR. The ECU then controls drive actuator 600 so that cartridge 202 is rotated and selected strip 501 is placed in injection zone ZI. The choice of strip 501 may depend on the analysis desired (if different types of strips are placed in the cartridge 202) by the user, or may be made automatically (strips used successively according to a pre-established program). The ECU again retrieves data from position sensor 624 to ensure that the desired strip is correctly positioned. The absolute position of the strip may be determined using the position sensor (see above and below in the description). The exact positioning of the strip is done using the position sensor as described. A specific procedure will be described later. Step E2 may take a few seconds. However, as the urine has already been collected in step E1, there is no risk of missing the user's urination.

Step E3 ("urine injection") then involves positioning the urine analysis device in an injection position and injecting urine. The ECU controls the displacement actuator 620 so that the injector moves into the injection position PI. The distal end 700 then pierces the lid 511 of cartridge 202. The ECU then controls pump 614 to inject urine onto a test strip. The injected urine may then react with the reagents on the test strip. After the actual injection, injector 604 may be retracted to the withdrawal position PR.

Step E4 ("measure") is a measurement step that consists of obtaining data on the desired strip with the analyzer 606, 1200. To this end, the ECU drives the analyzer 606, 1200 to generate strip data. Step E4 may be carried out in parallel with step E3, a little before step E3, or a little after (particularly in relation to the injection of the first drop of urine). Obtaining data as soon as the first drop is injected enables reaction kinetics data to be obtained. Alternatively, only static data (when the strip reaction has stabilized) is used. When the analysis zone ZA and the injection zone ZI of the annular housing coincide (i.e. when analyzer 606, 1200 is positioned radially at the same place as injector 604), the ECU does not need to rotate cartridge 202.

Step E5 ("purge") involves purging the urine analysis device. The ECU drives the drive actuator 600 to align the purge opening 514 with the injector 604, then drives the displacement actuator 620 to move the injector to the purge position PP, then activates the pump 614 to push air. Urine is then expelled from the urinal via the purge channel and drain port 310. The urine analysis device 100 is thus in the same position as in step E0. Before the purge opening 514 is aligned with the injector 604, the injector 604 may be returned to the withdrawal position PR by driving the displacement actuator 620, if this has not been done at the end of step E3.

Activation of step E1 may involve the ECU receiving a request for urine analysis. The analysis request may come from the remote activator. The analysis request may also be ordered from the smartphone 114. The analysis request may also be made automatically, when the user is close to the toilet.

Similarly, activation of step E1 may imply that the ECU detects urine in the vicinity of the collection port 218. If no urine stream is received within a specified time, then the urine analysis device returns to step E0. If, on the other hand, a stream of urine is detected, step E1 is implemented.

Urine injection in step E2 may take place in two stages. For example, the automated syringe 80 may inject between 2.5 microliters and 3.5 microliters twice. This solution takes into account the reaction and migration time of the urine on the test strip 501.

The analyzer performs a colorimetric analysis on the test strip. The urine analysis device deduces the analysis result (s). The analysis performed depends on the type of test strip.

The analysis performed may also depend on a choice made by the user. The analysis performed may also depend on the user identified.

A step E6 for processing data and transmitting the result(s) may be implemented. The ECU processes the data received by the analyzer 606 and instructs a transmitter to transmit the result(s), for example directly to the user's mobile terminal 114. The result(s) may also be sent to server 116. The user can, for example, view and evaluate the result(s) on the smartphone 114 application, or on a website. The result(s) may also be sent to a healthcare professional. Step E6 may be performed at any time after step E4.

Steps E2 to E4 may be repeated several times. In this way, several test strips receive urine and are analyzed. So, several analyses may be performed from a single urine aspiration in step E1.

Step E0 consists of holding the urine analysis device in the purge position, by placing injector 604 in the purge position PP.

Figure 16:
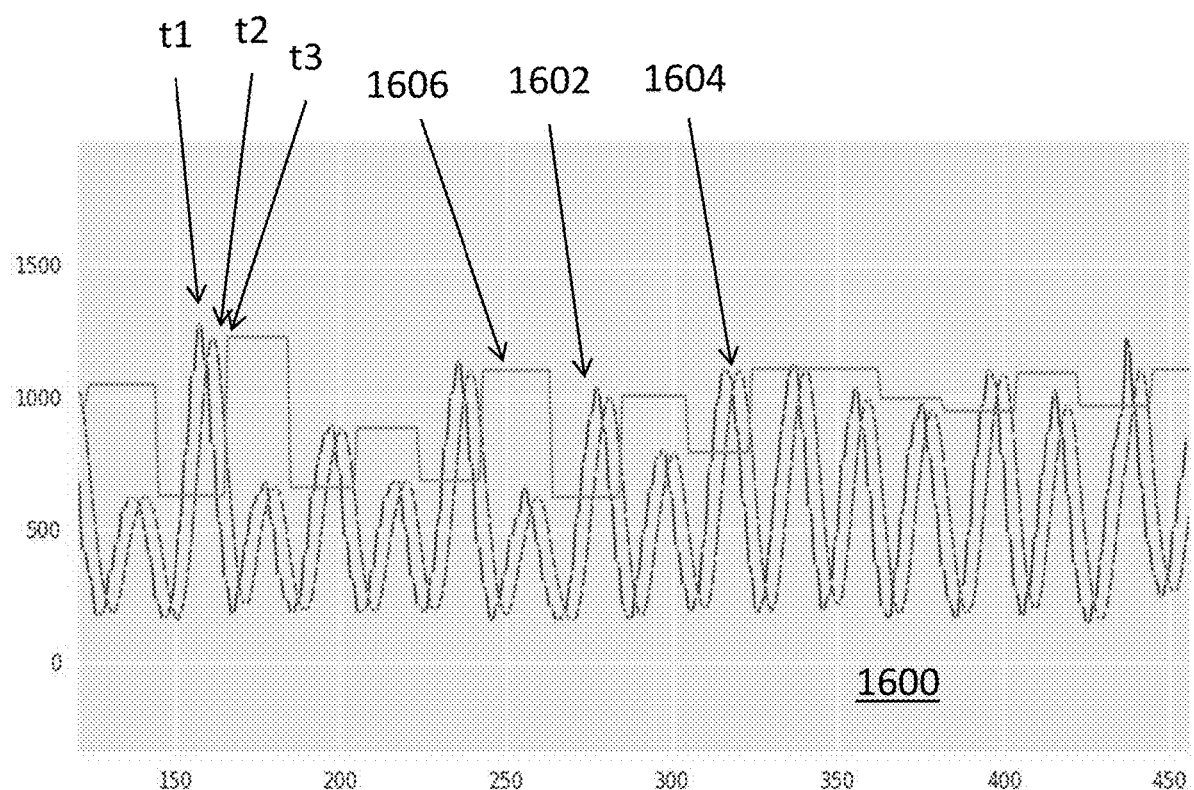
FIG. 16 This figure shows a graph with position sensor data.
Figure 17:
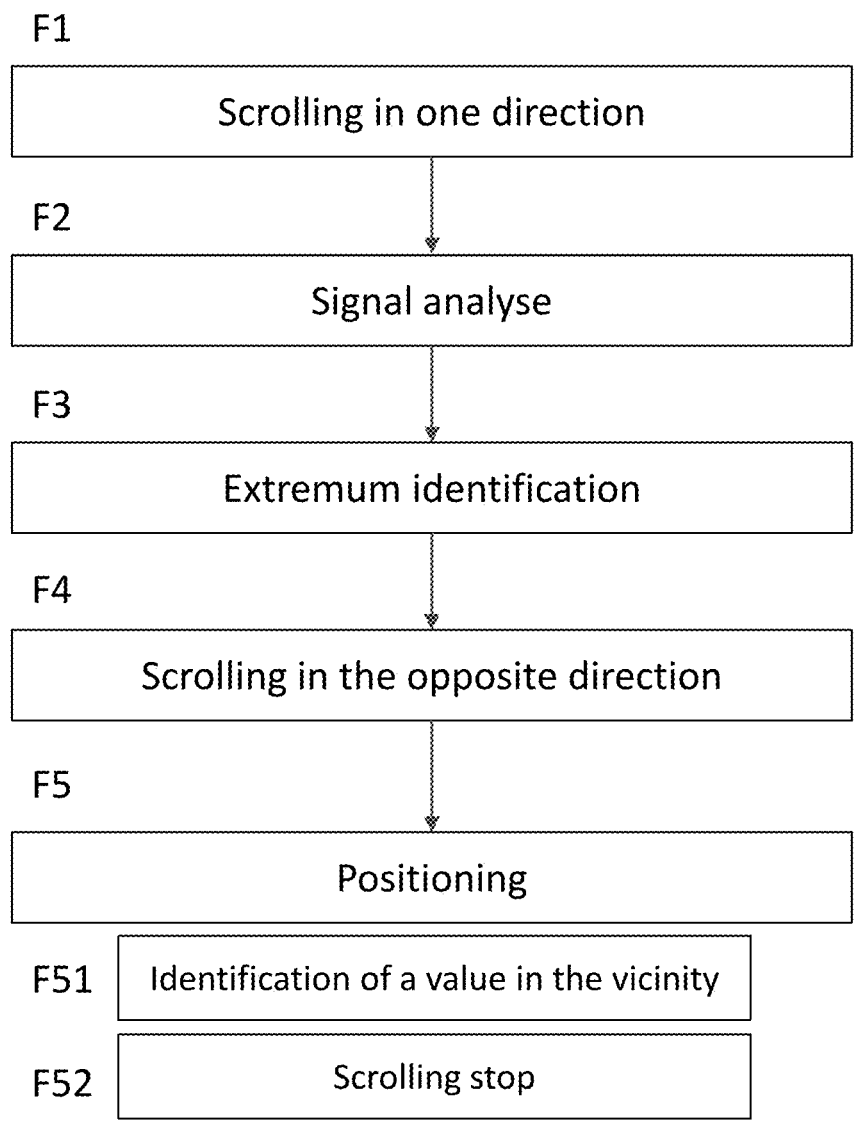
FIG. 17 This figure shows the steps involved in positioning the test strip in the injection or analysis zone of the urine analysis device.

The positioning of the strip will now be described in more detail. As previously indicated, position sensor 624 may receive a signal (e.g. a light signal) whose intensity varies as a function of the elements passing in front of the position sensor 624. In particular, the signal reaches an extremum when a strip is in the control zone ZC, i.e. radially facing the position sensor 624. In the case of a stepper motor 600, a signal value is determined for each step. The graph 1600 in FIG. 16 shows three curves: the signal 1602 obtained by the position sensor 624, the filtered signal 1604 (typically an average of several values) and the value 1606 of the last extremum. The ordinate is a unit of intensity of the optical signal and the abscissa is a number of steps of the drive motor 600. The higher intensities correspond to an alignment of the orifices 512 of the separator 508 with the position sensor 624, and the lower intensities correspond to the separator 508 blocking the light.

In an F1 step, the ECU sets the strips 501 in motion in a given direction, as they move past the position sensor 624. For example, the ECU may drive the motor 600 in one direction. The strips 501 may run past the position sensor 624 in two opposite directions. One direction is selected in step F1.

In a step F2, generally concomitant with step F1, the ECU receives and analyzes the evolution of the feedback signal during scrolling. A measurement may be obtained at each step of the drive motor 600 or at regular time intervals (e.g. every 0.1 second), for example if the motor is continuously moving.

In step F3, the ECU identifies a local signal extremum. This means that the ECU has detected that the signal value has started to decrease after a peak (to the nearest sign). In this respect, the ECU needs to detect at least three signal values, corresponding to three different cartridge positions, for which the intermediate value is the highest (to the nearest sign) of the three values. These three values may be detected over three successive steps, for example.

More generically (in the case of a stepper motor), if we assume that there is an extremum at step N (time t1, or t2 for the filtered signal, on FIG. 16), the ECU observes a window of ±k measurements (i.e. 2xk+1steps), and if value[N]=max (value[N−k;N+k]), the ECU determines that value[N] is an extremum (time t3 on FIG. 16). Nevertheless, the cartridge is now in position N+k, i.e. the extremum of position N has been exceeded by k steps at this point. One solution is to go back k steps. On the other hand, as the drive chain has backlash, the ECU cannot simply count k steps in the other direction: the ECU seeks to find the value of the extremum (modulo a margin), which means that the cartridge is in the desired position. Steps F4 and F5 describe this in detail.

In a step F4, in response to step F3, the ECU sets the strips in motion in the opposite direction to that of step F1. For example, the ECU may drive the motor 600 in the other direction, or cause a reversal of the direction of rotation in the gear chain 608 (by disengaging or engaging a gear).

In step F5, the ECU positions the strip that has generated the extremum. In other words, the ECU stops the drive actuator 600 to position the strip at the desired location, which in this case is the injection zone ZI or the analysis zone ZA (which may be confused, as explained above). In particular, when the control zone ZC is confused with the injection zone ZI and/or the analysis zone ZA, the desired location is the control zone ZC, i.e. the zone facing the position sensor 624. Step F5 may comprise a sub-step F51 in which the ECU identifies a signal value close to the value of the first local extremum, and a sub-step F52 in which scrolling is stopped in the opposite direction. By "close" it is meant a value that is identical or similar to within a predetermined deviation (defined, for example, during testing). When a close value is identified, scrolling is stopped at the position corresponding exactly to the extremum. If the ECU were to determine a new extremum, the reverse scrolling would have to go beyond the position corresponding to the original extremum.

In reverse scrolling (step F4), i.e. when the ECU is trying to find the cartridge position corresponding to the extremum, scrolling may take place at the same speed as in the direction of step F1, in order to have the same acquisition conditions as in steps F1 and F2. For this, step-by-step movement is particularly suitable.

When the ECU detects an extremum, the cartridge 202 has been rotated by only a few degrees, so that no other strip has yet passed the position sensor 624, or at least no other extremum may be identified.

Firstly, measuring the strip position directly eliminates the inaccuracies of backlash in the mechanical chain (e.g. the backlash between the gear train pinions 608 when changing direction of rotation) and of the strip position (see FIG. 13). Moreover, identifying an extremum makes it possible to avoid variations in signal values between strips. As shown in graph 1600, extrema values may vary. Two successive extremums (associated with two successive strips) may therefore have different values without the process failing. Extrema deviations may arise from irregularities in strip positioning, or from the nature of the strips themselves (a cartridge 202 may incorporate different types of strips, which do not present the same response to the optical sensor, all other parameters being equal). Secondly, the process makes it possible to manage the latency of data processing by the electronics (position sensor and ECU): the fact that the peak is not known in real time is compensated for by displacement in the opposite direction. On-board electronics may therefore be less power-consuming, less expensive and more robust.

It should be noted here that this process may be implemented independently of the annular shape of the housing 212. However, the rotational movement of cartridge 202 in station 200 is particularly well-suited to this type of process, for all the strips in the cartridge (due to the symmetry of rotation).

In reference to counting the strips to identify which strip is in the control zone, the ECU may count the extremums that the position sensor has seen scroll by. For example, if the ECU determines that strip number 54 should be used (out of 90, for example), the ECU may count 90 extremums from zero.

Additional Information on Test Media

The test supports comprise a reagent that reacts on contact with urine. In an embodiment, the reagent is a dry reagent. In particular, the test supports are test strips, which will be described in more detail below.

Test strips 501 may be of the lateral or vertical flow immunoassay type. In this case, test strips 501 comprise a sample buffer and an absorption buffer. A nitrocellulose membrane extends between the sample pad and the absorption pad. So, when a urine sample is introduced onto the sample pad, it migrates by capillary action to the absorption pad, passing through a conjugate pad, one or more test lines, and a control line. The conjugate pad, test line(s) and control line contain reagents.

The conjugate pad contains detection antibodies sensitive to compounds in the urine. If the compounds are present when the urine sample passes through the conjugate pad, then the antibodies bind to the compounds to form markers. The markers migrate to a test line. The test line includes test antibodies. The test antibodies bind with the markers and retain them on the test line. This forms a colored line, the density of which varies according to the concentration of markers present. The remaining sample migrates to a control line. The control line contains control antibodies, indicating that the sample has passed through the nitrocellulose membrane.

For example, test strips may be ELISA-type strips. This type of test strip enables detection of the pregnancy hormone hCG in urine. In this case, the detection antibody may be "mouse monoclonal beta hCG", the test antibody may be "goat poluclonal anti-mouse IgG" and the control antibody may be "rabbit polyclonal anti-mouse igG".

Test strips may be conventional colorimetric strips. In this case, each test strip comprises at least one pad containing one or more reagents sensitive to one or more compounds contained in the urine sample. For example, the compound (s) may be: LH hormone, HCG hormone, leukocytes/nitrites, urobilinogen/bilirubin, proteins, pH, specific gravity and/or glucose.

Other types of reaction may use reagents or compounds designed to detect the presence of a particular analyte (e.g. Molecularly imprinted polymers or MIPs), including a drug active ingredient or drug active ingredient metabolite in urine. In this case, the device may be used to monitor a user's compliance with a drug treatment, in particular to check that he is taking his treatment properly or to alert him when he has failed to take it.

Each test strip is generally rectangular. A width of each test strip may be between 0.5 mm and 3 mm, for example about 1 mm. A length of each test strip may be between 10 and 15 mm, for example 12 mm or about 12 mm. Alternatively, each test strip may have any shape, for example square or circular. The shape and dimensions of the test strips enable a large number of test strips to be stored in the urine analysis device (at least 50 strips, or even at least 100 strips). In fact, it appears possible to store up to 120 test strips, which corresponds to 4 months of analyses when a user performs one analysis per day.

The test result(s) may be one or more of the following: fertility, pregnancy, urinary tract infections, liver problems, kidney failure, uric lithiasis, dehydration, heart disease and/ or diabetes. The result(s) may also be an indicator of medication compliance.

The following clauses present various embodiments in accordance with the present description.

A1. A station (200) for a urine analysis device (100), the station comprising:
 a case (204), intended to be positioned inside a toilet (102),
 an annular housing (212), about an axis of rotation (A), in the case (204), the annular housing (212) being configured to at least partially receive a cartridge (202) rotatably mounted about the axis of rotation (A) in the station (200) and comprising a plurality of test supports (501),
 an injector (604), positioned in the case (204) and radially internal to the annular housing (212), the injector being configured to inject a controlled volume of urine onto at least one test support, the injector being mounted for translational movement relative to the case, in which the injector comprises a distal injection end whose translational displacement is in a radial or substantially radial direction relative to the axis of rotation.

A2. The station according to clause A1, in which:
 the injector (604) is driven in translation at a first translation axis (T1),
 the distal injection end (700) moves in translation along a second axis (T2), known as the injection axis, and
 the first translation axis (T1) is not coincident with the second axis (T2), when the latter are projected in a plane orthogonal to the axis of rotation (A).

A3. The station according to any one of clauses A1 to A2, in which the injector (604) is curved.

A4. The station according to any one of clauses A1 to A3, in which the case (204) comprises a central mechanical coupler (602), on the axis of rotation (A), able to cooperate with the cartridge (202) for rotating the latter.

A5. The station according to clause A4, in which the curved shape of the injector bypasses the mechanical coupler.

A6. The station according to any of clauses A1 to A5, wherein "substantially radial" means less than 5° either side of the radial direction, or even less than 2°.

A7. The station according to any one of clauses A1 to A6, in which:
 the injector comprises a proximal end (702), opposite the distal end (700), and configured to receive urine,
 the distal end (700) and the proximal end (702) are interconnected by an intermediate portion (710) comprising two successive inverted bends (706, 708).

A8. The station according to clause A7, wherein the bend (706) closest to the distal end (700) has a smaller radius of curvature than the bend (708) closest to the proximal end (708).

A9. The station according to any one of clauses A1 to A8, wherein the injector (604) is rigid.

A10. The station according to any of clauses A1 to A9, further comprising a displacement actuator (620), configured to displace the injector (604) in translation.

A11. The station according to clause A10, in which the injector is integral with a nut (800) able to receive a threaded rod driven in rotation by the displacement actuator (620).

A12. The station according to any of clauses A1 to A11, in which the injector (604) is mounted on a carriage (900).

A13. The station according to clause A11 and clause A12, in which the carriage takes up the forces transmitted by the displacement actuator (620).

A14. The station according to any one of clauses A1 to A13, wherein:
- the case comprises a urine collector, the collector being fluidly connected to the injector, in particular via the proximal end,
- comprising an electronic control unit, the electronic control unit (1402) being in the case (204),
- further comprising an analyzer (1200), positioned at least partially radially outside the annular housing and configured to optically analyze at least one test support,
- the analyzer is positioned facing the distal end of the injector, when projected in a plane orthogonal to the axis of rotation.

A15. A urine analysis device (100) comprising a station (200) according to any of the preceding clauses and a cartridge (202), the cartridge being configured to be at least partially received in the annular housing of the case.

B1. A station (200) for a urine analysis device (100), the station comprising:
- a case (204), intended to be positioned inside a toilet (102),
- an annular housing (212), about an axis of rotation (A), in the case (204), the annular housing being configured to at least partially receive a cartridge (202) mounted for rotation about the axis of rotation (A) in the station (200) and comprising a plurality of test supports (501),
- an injector (604), positioned in the case (204), and configured to inject a controlled volume of urine onto a test support (501), when the support is positioned in an injection zone (ZI) of the annular housing (212),
- a position sensor (624), configured to obtain the position of a marker associated with a test support of the cartridge when the marker is positioned in the injection zone (ZI) or in a proximity zone close of the injection zone.

B2. The station according to clause B1, in which the proximity zone to the injection zone (ZI) corresponds to an angular sector of less than 30° on either side of the injection zone, or even less than 20°, or even less than 10°, or even less than 5°.

B3. The station according to any one of clauses B1 to B2, wherein the marker is a test support (501) directly, and in particular a test strip.

B4. The station according to any of clauses B1 to B3, wherein the injector (604) comprises an injection distal end (700) and the position sensor (624) is radially aligned with the injector distal end (700).

B5. The station according to any one of clauses B1 to B4, wherein the injector (604) is positioned radially internal to the annular housing (212).

B6. The station according to any of clauses B1 to B5, wherein the position sensor (624) is positioned at least partially radially outside the annular housing (212).

B7. The station according to any one of clauses B1 to B6, wherein the case comprises an analyzer configured to analyze at least one test support.

B8. The station according to clause B7, wherein the injector (604) is configured to inject into an injection zone (ZI) of the annular housing (212) and the analyzer is configured to measure data in an analysis zone (ZA), the injection zone (ZI) and the analysis zone (ZA) being coincident.

B9. The station according to clause B7 or clause B8, wherein the position sensor is the analyzer (1200).

B10. The station according to any one of clauses B1 to B9, wherein the position sensor comprises a cam follower or an electromagnetic module.

B11. The station according to any of clauses B1 to B10, in which the injector (604) and the position sensor (624) are located at the same angular position about the axis of rotation (A), but offset along a direction parallel to the axis.

B12. The urine analysis device (100) comprising a station (200) according to any of the preceding clauses and a cartridge (202), the cartridge being configured to be at least partially received in the annular housing of the case.

C1. A station (200) for a urine analysis device (100), the station comprising:
- a case (204), intended to be positioned inside a toilet (102),
- an annular housing (212) about an axis of rotation, positioned in the case, the annular housing (212) being configured to at least partially receive a cartridge (202) mounted for rotation about the axis of rotation in the station and comprising a plurality of test supports (501),
- an analyzer (606, 1200), mounted in the case (204), and configured to obtain information relating to the test support after injection of urine, when the test support is in an analysis zone (ZA) of the annular housing (212),
- an injector (604), mounted in the case (204), and configured to inject a controlled volume of urine onto a test support, when the test support is in an injection zone (ZI) of the annular housing, in which the analysis zone (ZA) and the injection zone (ZI) coincide.

C2. The station according to clause C1, in which the analyzer and injector are angularly located at the same place around the axis of rotation (A).

C3. The station according to any of clauses C1 to C2, further comprising a position sensor (624), configured to obtain the position of a marker associated with a test support of the cartridge, when the marker is positioned in the analysis zone (ZA) or in a proximity zone of the analysis zone.

C4. The station according to clause C3, in which the proximity zone of the analysis zone (ZA) corresponds to an angular sector of minus 30° on either side of the injection zone, or even 20°, or even 10°, or even 5°.

C5. The station according to any one of clauses C1 to C4, wherein the analysis zone (ZA) corresponds to an angular sector including a single test support.

C6. The station according to any of clauses C1 to C5, in which the injector is mounted so as to be translatable in the case.

C7. The station according to any one of clauses C1 to C6, comprising a memory (1406) and a processor (1404), the memory comprising instructions configured to implement the following steps:
- (E3) injection of urine onto a test support by the injector (604),
- (E4) measurement on a test support by the analyzer (606, 1200).

C8. The station (200) according to clause C7, wherein the instructions do not include rotating the cartridge between the injection step (E3) and the analysis step (E4).

C9. The station (200) according to clause C7 or clause C8, wherein the instructions comprise that the measuring step (E4) starts before the end of the injection step (E3), for example two seconds before the end or as soon as the first drop of urine is injected, or even before the first drop of urine is injected.

C10. A urine analysis device (100) comprising a station (200) according to any of the preceding clauses and a cartridge (202), the cartridge being configured to be at least partially received in the annular housing of the case.

C11. Urine analysis method operating the urine analysis device according to clause C10, comprising the following steps, implemented by the device:
(E3) injecting urine onto the test support,
(E4) measuring on the test support by the analyzer, wherein the cartridge is not rotated between the injection step and the analysis step.

D1. A station for a urine analysis device (100), the station comprising:
a case (204), intended to be positioned inside a toilet (102),
a housing (212), in the case (204), configured to at least partially receive a cartridge comprising a plurality of test supports (501), the cartridge being movably mounted inside the housing (212),
a position sensor (624), configured to directly measure the position of a test support (501) of the cartridge (202) relative to the case (204).

D2. The station according to clause D1, wherein the position sensor (624) comprises a light source (1202, 1204) and an optical sensor (1206), the light source being configured to emit light towards a test support and the optical sensor (1206) being configured to receive the light.

D3. The station according to any of clauses D1 to D2, comprising an analyzer, the analyzer operating in an analysis zone (ZA) of the housing (212), and the position sensor (624) is configured to directly measure the position of a test support located in the analysis zone (ZA).

D4. The station according to clause D3, wherein the analyzer (606, 1200) is the position sensor (624).

D5. The station (200) according to any one of clauses D1 to D4, wherein the housing is an annular housing (212), about an axis of rotation (A), in the case (204), the annular housing being configured to at least partially receive a cartridge (202) mounted for rotation about the axis of rotation (A) in the station (200).

D6. The station for a urine analysis device according to any one of clauses D1 to D5, in which the position sensor (624) sees test supports passing by when the cartridge (202) is set in motion, and is able to receive a signal which varies according to whether or not a test support is present facing the position sensor (624), the station (200) further comprising an electronic control unit (1402) with a processor (1404) and a memory (1406), said memory comprising instructions which, when executed by the processor of the electronic control unit causes:
(F1) scrolling of the test supports in one direction,
(F2) analyzing the evolution of the signal during scrolling,
(F3) identifying a local extremum,
(F4) in response to said identifying, scrolling of the test supports in the opposite direction,
(F5) positioning of the test support which generated the first extremum.

D7. The station according to clause D6, wherein the positioning (F5) comprises:
after the test supports have been reversed (F4), (F51) identifying a value in the vicinity of the local extremum value,
(F52) stopping the reversal of the test supports.

D8. The station according to any one of clauses D1 to D7, in which the identification of the local extremum (F3) consists in successively obtaining at least three return signal values, corresponding to three different positions of the cartridge in the station and noting that the intermediate value is the highest, so that at the time of the identification of the local extremum, the test support is no longer facing the position sensor (624).

D9. The station according to any one of clauses D6 to D8, wherein the electronic control unit (1402) is in the case (204).

D10. The station according to any one of clauses D6 to D9, in combination with clause 5, wherein the scrolling is a rotation of the cartridge (202).

D11. The station according to any of clauses D1 to D10, wherein the case (204) comprises an injector (604), configured to inject urine onto the test support which is identified as being in position by the position sensor (624).

D12. The station (200) according to any one of clauses D1 to D11, comprising a stepping drive actuator, for driving the cartridge in displacement.

D13. The station (200) according to clause D12, wherein a signal value is obtained at each step.

D14. A urine analysis device (100) comprising a station (200) according to any of the preceding clauses and a cartridge (202), the cartridge being configured to be at least partially received in the annular housing of the case, each test support being integral with the cartridge and being configured to selectively scroll past the position sensor (624).

D15. The urine analysis device (100) according to clause D14, wherein the test support is a test strip.

D16. A method of positioning a test support using the device of clause D14, the method comprising a step of measuring the position of a test support directly.

D17. The method of positioning according to clause D16, in combination with the station of clause D6, the method comprising the following steps:
(F1) scrolling the test supports in one direction,
(F2) analyzing the evolution of the signal during scrolling,
(F3) identifying a local extremum,
(F4) in response to said identifying, scrolling the test supports in the opposite direction,
(F5) positioning the test support which generated the first extremum.

The invention claimed is:
1. A station for a urine analysis device, the station comprising:
a case intended to be removably positioned on an inner wall of a toilet bowl,
an annular housing positioned within the case, the annular housing being configured to at least partially receive a cartridge mounted for rotation about an axis of rotation within the station and comprising a plurality of test supports, an analyzer, mounted in the case, and configured to obtain information relating to a test support of the plurality of test supports after injection of urine, when the test support is in an analysis zone of the annular housing, an injector, mounted in the case, and configured to inject a controlled volume of urine onto the test support, when the test support is in an injection zone of the annular housing, wherein the analysis zone and the injection zone coincide.

2. The station according to claim 1, wherein the analyzer and injector are angularly located at a same point around the axis of rotation.

3. The station according to claim 1, further comprising a position sensor, configured to obtain a position of a marker associated with the test support of the plurality of test supports, when said marker is positioned in the analysis zone or in a proximity zone of the analysis zone.

4. The station according to claim 3, wherein the analysis zone or the proximity zone corresponds to an angular sector of minus 30° on either side of the injection zone.

5. The station according to claim 4, wherein the analysis zone or the proximity zone corresponds to an angular sector of minus 20° on either side of the injection zone.

6. The station according to claim 5, wherein the analysis zone or the proximity zone corresponds to an angular sector of minus 10° on either side of the injection zone.

7. The station according to claim 6, wherein the analysis zone or the proximity zone corresponds to an angular sector of minus 5° on either side of the injection zone.

8. The station according to claim 1, comprising a memory and a processor, said memory comprising instructions configured to implement the following steps:
   injection of urine onto the test support by the injector,
   measurement on the test support by the analyzer.

9. The station according to claim 8, wherein the instructions do not include rotating the cartridge between the injection step and the measurement step.

10. The station according to claim 8, wherein the instructions comprise instructions for starting the measurement step before an end of the injection step.

11. The station according to claim 10, wherein the instructions specify that the measurement step starts at least two seconds before the end of the injection step.

12. The station according to claim 11, wherein the instructions specify that the measurement step starts as soon as the first drop of urine is injected.

13. The station according to claim 12, wherein the instructions specify that the measurement step starts before the first drop of urine is injected.

14. A urine analysis device comprising a station according to claim 1 and a cartridge, the cartridge being configured to be at least partially received in the annular housing of the case.

15. The urine analysis device according to claim 14, wherein the analysis zone corresponds to an angular sector including a single test support.

16. The urine analysis device according to claim 15, wherein the cartridge comprises a rotary support configured to be rotated by station, the cartridge comprising test strips attached to and integral with the rotary support, the strips being arranged parallel to one another.

17. A urine analysis method using the urine analysis device of claim 15, comprising the following steps carried out by the urine analysis device:
   injection of urine onto the test support by the injector,
   measurement on the test support by the analyzer,
wherein the cartridge is not rotated between the injection step and the measurement step.

18. The station according to claim 1, wherein the case has a diameter, measured in the direction normal to the axis of rotation, of between 50 mm and 150 mm.

19. The station according to claim 1, wherein the injector is mounted so as to be translatable in the case.

20. A station for a urine analysis device, the station comprising:
   a case intended to be positioned inside a toilet bowl,
   an annular housing positioned within the case, the annular housing being configured to at least partially receive a cartridge mounted for rotation about an axis of rotation within the station and comprising a plurality of test supports,
   an analyzer, mounted in the case, and configured to obtain information relating to a test support the plurality of test supports after injection of urine, when the test support is in an analysis zone of the annular housing,
   an injector, mounted in the case, and configured to inject a controlled volume of urine onto the test support, when the test support is in an injection zone of the annular housing,
   wherein the analysis zone and the injection zone coincide, and
   wherein the injector is mounted so as to be translatable in the case.

21. The station according to claim 20, wherein the analyzer and injector are angularly located at a same point around the axis of rotation.

22. A station for a urine analysis device, the station comprising:
   a case intended to be positioned inside a toilet bowl,
   an annular housing positioned within the case, the annular housing being configured to at least partially receive a cartridge mounted for rotation about an axis of rotation within the station and comprising a plurality of test supports,
   an analyzer, mounted in the case, and configured to obtain information relating to a test support the plurality of test supports after injection of urine, when the test support is in an analysis zone of the annular housing,
   an injector, mounted in the case, and configured to inject a controlled volume of urine onto the test support, when the test support is in an injection zone of the annular housing,
   wherein the analysis zone and the injection zone coincide, and
   wherein the case has a diameter, measured in the direction normal to the axis of rotation, of between 50 mm and 150 mm.

23. The station according to claim 22, wherein the analyzer and injector are angularly located at a same point around the axis of rotation.

* * * * *